US012582589B2

(12) United States Patent
Khine et al.

(10) Patent No.: US 12,582,589 B2
(45) Date of Patent: Mar. 24, 2026

(54) COMPOSITIONS AND METHODS FOR EYELASHES

(71) Applicant: L'OREAL, Paris (FR)

(72) Inventors: Cho-Cho Khine, Bridgewater, NJ (US); Ronak Rughani, Edison, NJ (US); Rachel Ferebee Maher, Morristown, NJ (US); Brady Zarket, Union, NJ (US); Siva Muthukrishnan, Bridgewater, NJ (US); Aakash Parekh, Edison, NJ (US)

(73) Assignee: L'Oréal, Paris (FR)

( * ) Notice: Subject to any disclaimer, the term of this patent is extended or adjusted under 35 U.S.C. 154(b) by 0 days.

(21) Appl. No.: 17/131,335

(22) Filed: Dec. 22, 2020

(65) Prior Publication Data

US 2021/0196594 A1 Jul. 1, 2021

Related U.S. Application Data

(60) Provisional application No. 62/953,873, filed on Dec. 26, 2019.

(51) Int. Cl.

| | |
|---|---|
| ***A61K 8/37*** | (2006.01) |
| ***A61K 8/25*** | (2006.01) |
| ***A61K 8/73*** | (2006.01) |
| ***A61K 8/81*** | (2006.01) |
| ***A61K 8/87*** | (2006.01) |

(Continued)

(52) U.S. Cl.

CPC ................ *A61K 8/375* (2013.01); *A61K 8/25* (2013.01); *A61K 8/73* (2013.01); *A61K 8/733* (2013.01); *A61K 8/8147* (2013.01); *A61K 8/87* (2013.01); *A61K 8/965* (2013.01); *A61Q 1/10* (2013.01);

(Continued)

(58) Field of Classification Search

CPC .... A61K 8/602; A61K 2800/43; A61K 8/375; A61K 8/8129; A61K 8/8147; A61K 8/368; A61K 8/733; A61K 8/73; A61K 2800/48; A61K 8/87; A61K 8/25; A61K 8/8164; A61K 8/965; A61Q 1/10

See application file for complete search history.

(56) References Cited

U.S. PATENT DOCUMENTS

| | | |
|---|---|---|
| 2,047,398 A | 7/1936 | Voss et al. |
| 2,102,113 A | 12/1937 | Djordjevitch |

(Continued)

FOREIGN PATENT DOCUMENTS

| | | |
|---|---|---|
| CN | 1422143 A | 6/2003 |
| CN | 1452477 A | 10/2003 |

(Continued)

OTHER PUBLICATIONS

Co-pending U.S. Appl. No. 17/130,273, filed Dec. 22, 2020.

(Continued)

*Primary Examiner* — Jianfeng Song

(74) *Attorney, Agent, or Firm* — The Marbury Law Group, PLLC

(57) ABSTRACT

The disclosure relates to mascara compositions and methods for making up the eyelashes. The compositions comprise at least one polyphenol or combinations of at least one polyphenol and at least one film forming polymer or at least one polyphenol, at least one film forming polymer, and at least one thickener. The methods comprise applying the mascara compositions to the eyelashes.

13 Claims, 4 Drawing Sheets

(51) Int. Cl.
*A61K 8/96* (2006.01)
*A61Q 1/10* (2006.01)

(52) U.S. Cl.
CPC ...... *A61K 2800/43* (2013.01); *A61K 2800/48* (2013.01)

(56) References Cited

U.S. PATENT DOCUMENTS

| | | | |
|---|---|---|---|
| 2,723,248 | A | 11/1955 | Wright |
| 3,579,629 | A | 5/1971 | Pasero et al. |
| 3,589,978 | A | 6/1971 | Kamal et al. |
| 3,734,874 | A | 5/1973 | Kibler et al. |
| 3,779,993 | A | 12/1973 | Kibler et al. |
| 3,810,977 | A | 5/1974 | Levine et al. |
| 3,836,537 | A | 9/1974 | Boerwinkle et al. |
| 3,910,862 | A | 10/1975 | Barabas et al. |
| 3,946,749 | A | 3/1976 | Papantoniou |
| 3,966,403 | A | 6/1976 | Papantoniou et al. |
| 3,966,404 | A | 6/1976 | Papantoniou et al. |
| 4,031,307 | A | 6/1977 | DeMartino et al. |
| 4,119,680 | A | 10/1978 | Vachon |
| 4,128,631 | A | 12/1978 | Lundmark et al. |
| 4,131,576 | A | 12/1978 | Iovine et al. |
| 4,137,180 | A | 1/1979 | Naik et al. |
| 4,137,208 | A | 1/1979 | Elliott |
| 4,165,367 | A | 8/1979 | Chakrabarti |
| 4,282,203 | A | 8/1981 | Jacquet et al. |
| 4,289,752 | A | 9/1981 | Mahieu et al. |
| 4,300,580 | A | 11/1981 | O'Neill et al. |
| 4,517,175 | A | 5/1985 | Iwabuchi et al. |
| 4,693,935 | A | 9/1987 | Mazurek |
| 4,728,571 | A | 3/1988 | Clemens et al. |
| 4,874,554 | A | 10/1989 | Lange et al. |
| 4,972,037 | A | 11/1990 | Garbe et al. |
| 4,973,656 | A | 11/1990 | Blount |
| 5,198,217 | A | 3/1993 | Vedros |
| 5,538,717 | A | 7/1996 | La Poterie |
| 5,660,816 | A | 8/1997 | Adams et al. |
| 5,660,818 | A | 8/1997 | Dubief et al. |
| 5,662,893 | A | 9/1997 | George et al. |
| 5,674,479 | A | 10/1997 | George et al. |
| 5,686,082 | A | 11/1997 | N'Guyen |
| 5,792,448 | A | 8/1998 | Dubief et al. |
| 6,106,813 | A | 8/2000 | Mondet et al. |
| 6,166,093 | A | 12/2000 | Mougin et al. |
| 6,214,329 | B1 * | 4/2001 | Brieva ..................... A61K 8/87 424/70.17 |
| 6,395,265 | B1 | 5/2002 | Mougin et al. |
| 6,482,942 | B1 | 11/2002 | Vittori |
| 7,151,079 | B2 | 12/2006 | Fack et al. |
| 8,551,503 | B2 | 10/2013 | Segura-Orsoni et al. |
| 10,052,273 | B2 | 8/2018 | Lalleman et al. |
| 10,327,999 | B2 | 6/2019 | Knappe et al. |
| 11,311,473 | B2 | 4/2022 | Fischer et al. |
| 2002/0034486 | A1 | 3/2002 | Midha et al. |
| 2003/0064038 | A1 * | 4/2003 | Auguste ................. A61K 8/044 424/401 |
| 2003/0175230 | A1 | 9/2003 | Dubief |
| 2004/0132699 | A1 * | 7/2004 | Zhuang ................... A61P 17/16 514/170 |
| 2006/0134049 | A1 | 6/2006 | Keenan et al. |
| 2007/0264220 | A1 | 11/2007 | Hiraishi et al. |
| 2008/0031841 | A1 | 2/2008 | Laurent et al. |
| 2008/0112897 | A1 | 5/2008 | Schiemann et al. |
| 2009/0042846 | A1 | 2/2009 | Gupta |
| 2012/0230925 | A1 | 9/2012 | Wagner et al. |
| 2013/0109746 | A1 | 5/2013 | Derkx et al. |
| 2013/0202546 | A1 | 8/2013 | Howell |
| 2013/0232701 | A1 | 9/2013 | Aimi et al. |
| 2014/0093466 | A1 | 4/2014 | Combs et al. |
| 2017/0340542 | A1 | 11/2017 | Lalleman et al. |
| 2017/0354584 | A1 | 12/2017 | Lalleman et al. |
| 2018/0104161 | A1 * | 4/2018 | Siddiqui ................ A61K 8/731 |
| 2018/0346653 | A1 | 12/2018 | Dussaud et al. |
| 2018/0353401 | A1 | 12/2018 | Wossene et al. |
| 2019/0159995 | A1 | 5/2019 | Ebanks et al. |
| 2019/0224093 | A1 | 7/2019 | Furukawa et al. |
| 2019/0314252 | A1 | 10/2019 | Iwatani et al. |
| 2020/0129407 | A1 | 4/2020 | Noll et al. |

FOREIGN PATENT DOCUMENTS

| | | | |
|---|---|---|---|
| CN | 104257544 | A | 1/2015 |
| CN | 106511104 | A | 3/2017 |
| CN | 106821840 | A | 6/2017 |
| CN | 109562033 | A | 4/2019 |
| CN | 110123668 | A | 8/2019 |
| CN | 110300573 | A | 10/2019 |
| CN | 110820336 | A | 2/2020 |
| DE | 2330956 | A1 | 1/1974 |
| EP | 0412704 | A2 | 2/1991 |
| EP | 0412707 | A1 | 2/1991 |
| EP | 0507272 | A1 | 10/1992 |
| EP | 0582152 | A2 | 2/1994 |
| EP | 0619111 | A1 | 10/1994 |
| EP | 0637600 | A1 | 2/1995 |
| EP | 0640105 | A1 | 3/1995 |
| EP | 0648485 | A1 | 4/1995 |
| EP | 0656021 | A1 | 6/1995 |
| EP | 0680744 | A1 | 11/1995 |
| EP | 0751162 | A1 | 1/1997 |
| EP | 1927378 | A1 | 6/2008 |
| EP | 3403642 | A1 | 11/2018 |
| FR | 1222944 | A | 6/1960 |
| FR | 1564110 | A | 4/1969 |
| FR | 1580545 | A | 9/1969 |
| FR | 2077143 | A5 | 10/1971 |
| FR | 2198719 | A1 | 4/1974 |
| FR | 2265781 | A1 | 10/1975 |
| FR | 2265782 | A1 | 10/1975 |
| FR | 2350384 | A1 | 12/1977 |
| FR | 2357241 | A2 | 2/1978 |
| FR | 2393573 | A1 | 1/1979 |
| FR | 2439798 | A1 | 5/1980 |
| FR | 2743297 | A1 | 7/1997 |
| FR | 2892625 | A1 | 5/2007 |
| FR | 2956809 | A1 | 9/2011 |
| FR | 2981569 | A1 | 4/2013 |
| FR | 3059900 | A1 | 6/2018 |
| GB | 839805 | A | 6/1960 |
| GB | 922457 | A | 4/1963 |
| GB | 1408388 | A | 10/1975 |
| GB | 1572626 | A | 7/1980 |
| JP | 3966825 | B2 | 8/2007 |
| JP | 2008-247761 | A | 10/2008 |
| JP | 2012-214453 | A | 11/2012 |
| JP | 2013-053086 | A | 3/2013 |
| JP | 2019-202968 | A | 11/2019 |
| KR | 10-2010-0026712 | A | 3/2010 |
| LU | 75370 | A1 | 2/1978 |
| LU | 75371 | A1 | 2/1978 |
| TW | 201400133 | A | 1/2014 |
| WO | 93/23009 | A1 | 11/1993 |
| WO | 93/23446 | A2 | 11/1993 |
| WO | 94/03510 | A1 | 2/1994 |
| WO | 95/00578 | A1 | 1/1995 |
| WO | 95/18191 | A1 | 7/1995 |
| WO | 97/08261 | A1 | 3/1997 |
| WO | 97/20899 | A1 | 6/1997 |
| WO | 0191705 | A1 | 12/2001 |
| WO | 2013131756 | A2 | 9/2013 |
| WO | 2014/102251 | A2 | 7/2014 |
| WO | 2014145057 | A1 | 9/2014 |
| WO | 2019/197852 | A1 | 10/2019 |
| WO | 2019/200027 | A1 | 10/2019 |
| WO | 2019195900 | A1 | 10/2019 |
| WO | 2019195901 | A1 | 10/2019 |

(56) References Cited

FOREIGN PATENT DOCUMENTS

WO 2019212710 A1 11/2019
WO 2021/133867 A1 7/2021

OTHER PUBLICATIONS

Lechocinski, N., et al., "Fiber orientation measurement using polarization imaging," J. Cosmet. Sci., 62, (Mar./Apr. 2011), pp. 85-100.
Mintel: "Black Eyelash Tint," Tana Cosmetics, XP055792645, Database accession No. 540089, Jun. 5, 2006, pp. 1-2.
International Search Report and Written Opinion for counterpart Application No. PCT/US2020/066763, dated Apr. 23, 2021.
International Search Report and Written Opinion for counterpart Application No. PCT/US2020/066939, dated Apr. 19, 2021.
Mintel: "Vivid Volume & Length Double Effect Mascara," Wei Ke Le Cosmetics, XP055792650, Database accession No. 5788913, Jun. 28, 2018.
Mintel: "Magical Fast-Drying Mascara," Magic Mirror Group, XP055792678, Database accession No. 5601775, Apr. 17, 2018.
Mintel: "Wax," Angfa, XP055795379, Database Accession No. 4548051, Jan. 12, 2017.
Non-Final Office Action for copending U.S. Appl. No. 17/130,273, dated Dec. 6, 2022.
International Search Report and Written Opinion for counterpart Application No. PCT/US2022/035722, dated Oct. 11, 2022.
Mintel: "Blowout Bombe, " Cuvée Beauty, Record ID 6184235, XP055966277, Dated Dec. 17, 2018.
Mintel: "Spun Satin Feather Light Styling Souffle," TIGI, Record ID 1210769, XP055966282, dated Nov. 11, 2009.
Mintel: "Texture Defining Lotion," Back to Basics Products, Record ID 690828, XP055966286, dated Apr. 13, 2007.
Co-pending U.S. Appl. No. 17/855,765, entitled: "Compositions and Methods for Styling Hair," Inventors: Vibha K. Shah et al., dated Jun. 30, 2022.
International Search Report and Written Opinion for counterpart Application No. PCT/US2022/035721, dated Oct. 13, 2022.
Mintel: "Cys-Treatment Straightening Hair Treatment," StylingLife Holdings, Record ID 1592789, XP055576886, dated Jun. 30, 2011.
Mintel: "BTX Hair Mask," Cedral Indústria de Cosméticos, Record No. 7121607, XP055755362, dated Dec. 20, 2019.
Mintel: "Lisoplastia Intense Straightening and Realigning of Hair Fiber," I Like Cosméticos, Record ID 8415629, XP055968116, dated Jan. 19, 2021.
Mintel: "Straight Hair Treatment," Mediplus, Record No. 6309843, XP055968002, dated Jan. 31, 2019.
Mintel: "Volume Control Mask," Garden Indústria e Comércio de Cosméticos; Record No. 4505773, XP055968006, dated Jan. 3, 2017.
Mintel: "Anti-Frizz Balm," Fekkai Brands; Record ID 5861079, XP055968148, dated Aug. 20, 2018.
Co-pending U.S. Appl. No. 17/853,580, entitled "Compositions and Methods for Styling Hair," inventors: Rachel Ferebee Maher et al., filed Jun. 29, 2022.
Co-pending U.S. Appl. No. 17/852,729, entitled "Compositions and Methods for Styling Hair," inventor: Vibha K. Shah, filed Jun. 29, 2022.
Co-pending U.S. Appl. No. 17/853,128, entitled "Compositions and Methods for Styling Hair," inventor: Vibha K. Shah, filed Jun. 29, 2022.
Co-pending U.S. Appl. No. 17/853,071, entitled "Compositions and Methods for Styling Hair," inventors: Vibha K. Shah et al., filed Jun. 29, 2022.
French Search Report and Written Opinion for counterpart French Application No. 2109872, dated Jun. 9, 2022.
Mintel: "Gold Fulvic Conditioner," Deciem, Record No. 4406127, XP055928358, Jan. 31, 2017.
French Search Report and Written Opinion for counterpart French Application No. 2109862, dated Jun. 9, 2022.
Mintel: "Sleek Flow Cherry & Lilac Styling Cream," I-ne, Record No. 8707019, XP055928346, May 13, 2021.
Mintel: "Smoothing Hair Treatment," Grown Alchemist, Record No. 6419291, XP055928395, Mar. 21, 2019.
French Search Report and Written Opinion for counterpart Application No. 2109867, dated Jun. 10, 2022.
Mintel: "Keratin Sealer," Davines, Record No. 7938505, XP055929517, dated Jul. 7, 2020.
French Search Report and Written Opinion for counterpart Application No. 2109871, dated Jun. 9, 2022.
Mintel: "Vegetarian Miracle Conditioner," Davines, Record No. 7910153, XP055929519, Jun. 30, 2020.
International Preliminary Report on Patentability for counterpart Application No. PCT/US2020/066763, dated Jul. 7, 2022.
International Preliminary Report on Patentability for counterpart Application No. PCT/US2020/066939, dated Jul. 7, 2022.
Translation of Office Action in CN202080090614.7, mailed Feb. 27, 2024, 17 pages.
Office Action in U.S. Appl. No. 17/853,071, mailed Nov. 14, 2024, 23 pages.
Chinese Office Action and Search Report for counterpart Application No. 202080089561.7, dated Jul. 20, 2023 (translation unavailable).
French Search Report for counterpart Application No. FR2209186, issued May 12, 2023.
French Search Report and Written Opinion for counterpart Application No. FR2211644, dated Jun. 6, 2023.
Mintel: "Anti-Frizz Cream," Anaber Cometicos Ind. E. Com, Record ID 778779, XP093050505, dated Oct. 26, 2007.
Mintel: "Breakage Strengthening Scalp Serum for Weak Hair," Niche Beauty Lab, Record ID 9764688, XP093050554, Aug. 9, 2022.
Mintel: "No. 6 Bond Smoother," Olaplex, Record ID 9746722, XP093050562, Jul. 14, 2022.
Final Office Action for copending U.S. Appl. No. 17/130,273, dated Aug. 2, 2023.
Non-Final Office Action for copending U.S. Appl. No. 17/853,071, dated Sep. 14, 2023.
Final Office Action in U.S. Appl. No. 17/855,765, mailed Sep. 13, 2024, 11 pages.
International Preliminary Report on Patentability in PCT/US2022/035722, mailed Dec. 14, 2023, 12 pages.
International Preliminary Report on Patentability in PCT/US2022/035721, mailed Dec. 14, 2023, 11 pages.
Non-Final Office Action in U.S. Appl. No. 17/855,765, mailed Jan. 17, 2024, 10 pages.
Office Action in CN202080089561.7, mailed Mar. 30, 2024, 12 pages.
Deffaugt-Sanchez, Coline. "Hair Care Advice at the Pharmacy: From Cosmetic Advice to Drug Treatments." Pharmaceutical Sciences (2011): 1-166.
Huanbutta et al. "Use of seed gums from Tamarindus indica and Cassia fistula as controlled-release agents." Asian journal of pharmaceutical sciences 13.5 (2018): 398-408.
Office Action in EP20841837.6, mailed Apr. 7, 2025, 8 pages.
Rao et al. "Effect of β-cyclodextrin on Rheological Properties of some Viscosity Modifiers." Indian Journal of Pharmaceutical Sciences 76.6 (2014): 545-548.
Yang, J. "Hair Care Cosmetics," Cosmetic science and technology: theoretical principles and applications. Elsevier (2017): 601-615.
Office Action in U.S. Appl. No. 17/855,765, mailed May 6, 2025, 10 pages.
Office Action in U.S. Appl. No. 17/853,580, mailed Feb. 26, 2025, 20 pages.
Non-Final Office Action for copending U.S. Appl. No. 17/853,128, dated Dec. 17, 2024.
Translation of Second Chinese Office Action for counterpart Application No. 202080090614.7, dated Dec. 25, 2024.
Non-Final Office Action for copending U.S. Appl. No. 17/852,729, dated Jan. 6, 2025.
Draelos, "Essentials of Hair Care often Neglected: Hair Cleansing," International Journal of Trichology, Jan.-Jun. 2010, vol. 2, Issue 1, pp. 24-29.

(56) References Cited

OTHER PUBLICATIONS

Non-Final Office Action for copending U.S. Appl. No. 17/853,580, dated Jul. 17, 2025.
Final Office Action for copending U.S. Appl. No. 17/853,128, dated Aug. 20, 2025.
Final Office Action for copending U.S. Appl. No. 17/853,071, dated Jun. 25, 2025.
Office Action in U.S. Appl. No. 17/852,729, mailed Dec. 17, 2025, 15 pages.
Office Action in U.S. Appl. No. 17/853,128, mailed Jan. 28, 2026, 18 pages.

* cited by examiner

COMPOSITIONS AND METHODS FOR EYELASHES

CROSS REFERENCE TO RELATED APPLICATION

This application claims the benefit of priority to U.S. Provisional Application No. 62/953,873 filed Dec. 26, 2019 which is incorporated by reference herein in its entirety.

TECHNICAL FIELD

The present disclosure relates to compositions and methods for making up eyelashes.

BACKGROUND

Makeup, such as mascara, is applied directly onto keratin fibers. As such, consumers desire more natural compositions for making up keratin fibers, including eyelashes. Synthetic chemicals and raw materials used in conventional makeup compositions are less desirable, and further may lack sustainable sourcing and therefore not comply with "green" manufacturing processes, which may also make the compositions less desirable to consumers. However, in order to enhance appearance, consumers seek mascara compositions that impart curl to the eyelashes.

Thus, there is a need for mascara compositions and methods wherein the compositions have desired cosmetic and composition properties with reduced amounts of synthetic chemicals compared to conventional mascara composition, which impart curl to the eyelashes at levels similar to or at a higher level than that of conventional mascara compositions.

SUMMARY

It has surprisingly been found that mascara compositions according to the disclosure provide curl and thickness to eyelashes that is comparable to or better than conventional mascara formulations, while allowing reduced amounts of synthetic chemicals or materials. For example, certain embodiments enable reduced amounts of film-forming polymer (e.g. up to ten times less), yet provide eyelash curl and thickness as well as, or better than, conventional mascara compositions comprising greater amounts of such polymers.

In one embodiment, the mascara compositions comprise (a) at least one polyphenol, and (b) at least one film forming polymer. In an embodiment, the pH of the composition is approximately at or below the pKa of the polyphenol.

In one embodiment, the mascara compositions comprise at least one film forming polymer present in an amount of about 0.001% to about 10%, about 0.01% to about 5%, about 0.05% to about 3%, or about 0.1% to about 2%, based on the total weight of the composition.

In an embodiment, the mascara compositions comprise at least one film forming polymer chosen from acrylate-based polymers, polyurethanes, polysaccharides, or mixtures thereof. In further embodiment, the mascara compositions comprise at least one film forming polymer chosen from PVM/MA Copolymer, carrageenan, gum Arabic, xanthan gum, oxidized inulin, chitosan, alginate, or mixtures thereof. The at least one film forming polymer may be chosen from PVM/MA (Poly(methyl vinyl ether-alt-maleic acid)(CAS Number 25153-40-6) or carrageenan.

In one embodiment, the mascara compositions comprise at least one polyphenol present in an amount ranging from about 0.1% to about 15%, about 1% to about 10%, or about 1% to about 5%, based on the total weight of the composition.

In one embodiment, the pH of the mascara compositions ranges from about 5 to about 8, about 5 to about 6.5, or about 5 to about 6.

In one embodiment, the mascara compositions comprise from about 50% to about 99% water by weight relative to the total composition.

In one embodiment, the weight ratio of the total amount of the polyphenol to the total amount of film forming polymer in the mascara compositions ranges from about 50:1 to about 1:1, about 20:1 to about 1:1, about 10:1 to about 1:1, about 7:1 to about 1:1, or about 5:1 to about 1:1.

In one embodiment, the mascara compositions comprise at least one thickener.

The mascara compositions may comprise at least one thickener present in an amount ranging from about 0.005% to about 5%, about 0.01% to about 3%, or about 0.05% to about 2%.

In a further embodiment, the weight ratio of the total amount of the polyphenol to the total amount of thickener ranges from about 50:1 to about 1:1, 20:1 to about 1:1, 10:1 to about 1:1, 7:1 to about 1:1, about 5:1 to about 1:1, or about 2:1 to about 1:1.

In a further embodiment, the at least one thickener is chosen from gums, water-soluble natural polymers, water-soluble synthetic polymers, clay minerals, silicic anhydride, or mixtures thereof. In an embodiment, the at least one thickener is algin.

In a further embodiment, the mascara compositions comprise:

at least one polyphenol which is tannic acid, and at least one film forming polymer of formula (I):

$$[CH_2CH(OCH_3)CH(CO_2H)CH(CO_2H)]n \quad (I),$$

wherein n is a number from about 2,500 to about 17,500, from about 3,000 to about 17,000, from about 3,500 to about 16,500, from about 4,000 to about 16,000, from about 4,500 to about 15,500, from about 5,000 to about 15,000, from about 5,500 to about 14,5000, from about 6,000 to about 14,000, from about 6,500 to about 7,000, from about 6,500 to about 13,500, from about 7,000 to about 13,000, from about 7,500 to about 12,500, from about 8,000 to about 12,000, or from about 8,500 to about 11,500, wherein the pH of the composition ranges from about 5 to about 6.5.

In a further embodiment, the mascara compositions comprise:

at least one polyphenol which is tannic acid, and at least one film forming polymer which is carrageenan, wherein the pH of the composition is from about 5 to about 6.5.

In an embodiment, the mascara compositions are substantially free of synthetic gums, silicones, or synthetic polymers. In an embodiment, at least 85% of the materials used in the mascara compositions are plant-based or of plant origin.

In a further embodiment, the mascara compositions comprise pigment.

The mascara compositions may comprise:

(a) at least one polyphenol, (b) at least one film forming polymer, and (c) at least one thickener, wherein the pH of the composition is approximately at or below the pKa of the polyphenol.

The mascara compositions may comprise:

(a) tannic acid, (b) at least one film forming polymer chosen from PVM/MA Copolymer, carrageenan, gum Arabic, xanthan gum, alginate, or mixtures thereof, and (c) algin, wherein the pH of the composition is approximately at or below the pKa of the polyphenol.

The mascara compositions may comprise:

(a) tannic acid, (b) at least one film forming polymer of formula (I):

$$[CH_2CH(OCH_3)CH(CO_2H)CH(CO_2H)]n,$$

wherein n is a number from about 2,500 to about 17,500, from about 3,000 to about 17,000, from about 3,500 to about 16,500, from about 4,000 to about 16,000, from about 4,500 to about 15,500, from about 5,000 to about 15,000, from about 5,500 to about 14,5000, from about 6,000 to about 14,000, from about 6,500 to about 7,000, from about 6,500 to about 13,500, from about 7,000 to about 13,000, from about 7,500 to about 12,500, from about 8,000 to about 12,000, or from about 8,500 to about 11,500, and (c) algin, wherein the pH of the composition is from about 5 to about 6.5.

The mascara compositions may comprise:

(a) tannic acid, (b) carrageenan, and (c) algin, wherein the pH of the composition is from about 5 to about 6.5.

In an embodiment, the methods for making up and/or enhancing the appearance of eyelashes comprise applying to the eyelashes a mascara composition comprising:

(a) at least one polyphenol, and (b) at least one film forming polymer, wherein the pH of the composition is approximately at or below the pKa of the polyphenol.

The methods for making up and/or enhancing the appearance of eyelashes may comprise:

(a) at least one polyphenol, (b) at least one film forming polymer, and (c) at least one thickener, wherein the pH of the composition is approximately at or below the pKa of the polyphenol.

The methods for making up and/or enhancing the appearance of eyelashes may comprise:

(a) tannic acid, (b) at least one film forming polymer chosen from PVM/MA Copolymer, carrageenan, gum Arabic, xanthan gum, alginate, or mixtures thereof, and (c) algin, wherein the pH of the composition is approximately at or below the pKa of the polyphenol.

The methods for making up and/or enhancing the appearance of eyelashes may comprise:

(a) tannic acid, (b) at least one film forming polymer of formula (I):

$$[CH_2CH(OCH_3)CH(CO_2H)CH(CO_2H)]n,$$

wherein n is a number from about 2,500 to about 17,500, from about 3,000 to about 17,000, from about 3,500 to about 16,500, from about 4,000 to about 16,000, from about 4,500 to about 15,500, from about 5,000 to about 15,000, from about 5,500 to about 14,5000, from about 6,000 to about 14,000, from about 6,500 to about 7,000, from about 6,500 to about 13,500, from about 7,000 to about 13,000, from about 7,500 to about 12,500, from about 8,000 to about 12,000, or from about 8,500 to about 11,500, and (c) algin, wherein the pH of the composition is from about 5 to about 6.5.

The methods for making up and/or enhancing the appearance of eyelashes may comprise:

(a) tannic acid, (b) carrageenan, and (c) algin, wherein the pH of the composition is from about 5 to about 6.5.

DESCRIPTION

Figure 1:
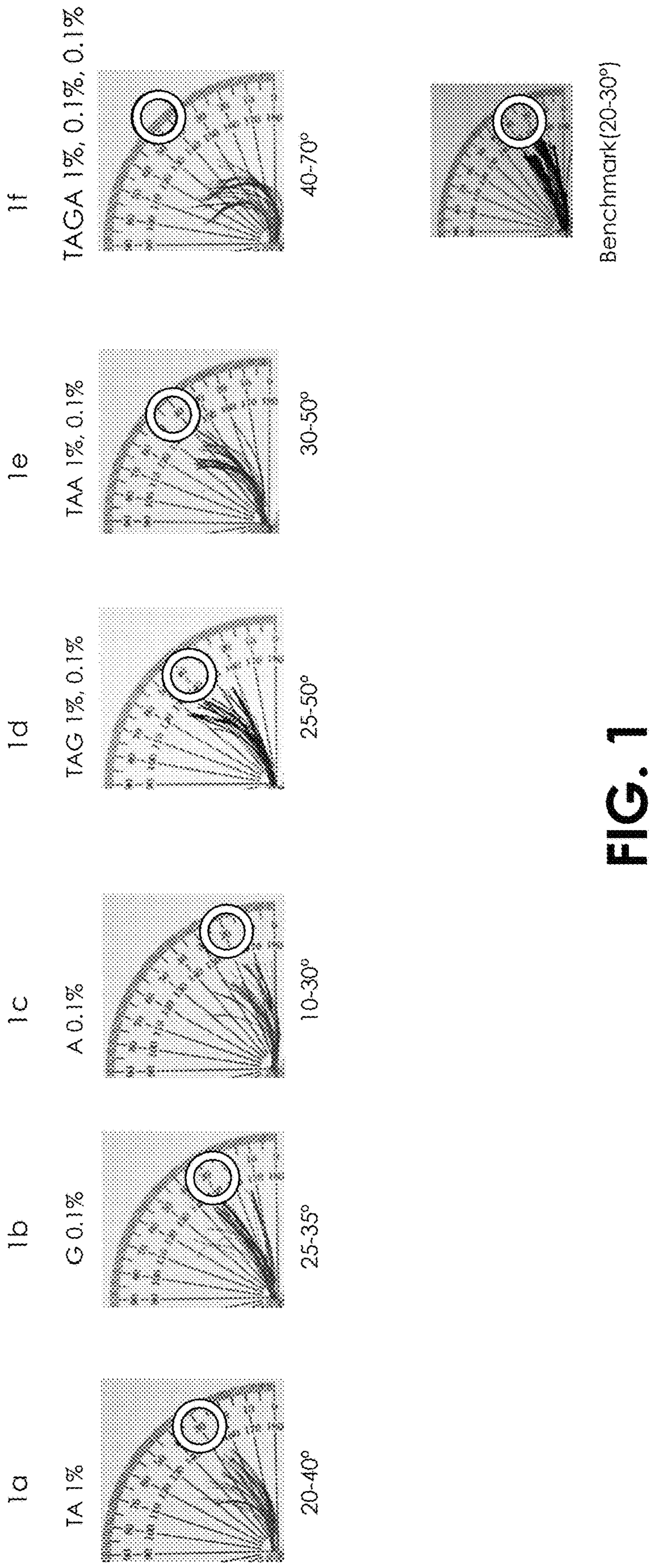
FIG. 1 shows photographs of eyelashes treated with compositions comprising tannic acid, Gantrez® PVM/MA, and/or algin. The eyelashes are aligned with a protractor to measure curliness of the eyelashes.

The disclosure relates to mascara compositions and methods for making up the eyelashes. The compositions comprise polyphenols, or synergistic combinations of polyphenols and polymers. The methods comprise applying the compositions to the eyelashes.

I. Compositions

The mascara compositions according to the disclosure comprise polyphenols or unexpectedly synergistic combinations of polyphenols and polymers, which surprisingly lead to improved eyelash curl.

Polyphenols

Mascara compositions according to the disclosure comprise at least one polyphenol. Polyphenols are phenols with more than one phenolic —OH group that have the ability to act as "donor molecules" by donating their alcoholic hydrogen or accepting delocalized electrons. The two classes of polyphenols are flavonoids and non-flavonoids.

Exemplary and non-limiting flavonoid compounds that can be used include: chalcones, such as phloretin, phloridzin, aspalathin, or neohesperidine; flavanols, such as catechin, fisetin, kaempferol, myricetin, quercetin, rutin, proanthocyanidins, pyroanthocyanidins, theaflavins, or thearubigins (or thearubrins); dihydroflavonols, such as astilbin, dihydroquercetin, or silibinin; flavanones, such as hesperidin, neohesperidin, hesperetin, naringenin, naringin, or poncirin; flavones, such as apigenin, baicalin, diosmin, or rhoifolin; anthocyanins, such as cyanidin, delphinidin, malvidin, peonidin, or petunidin; tannins, such as ellagitannins, tannic acid, gallic acid, or ellagic acid; isoflavonoids, such as biochanin A, Daidzein, or Genistein; fulvic acid, and neoflavanoids, as well as combinations thereof.

Exemplary and non-limiting non-flavonoid compounds that can be used include: Curcuminoids such as curcumin or tetrahydrocurcumin; Stibenoids such as astringin, resveratrol, or rhaponticin; Aurones such as bracteatin, or aureusidin; and Lignans such as pinoresinol, as well as combinations thereof.

Other polyphenols that can be used include hydroxycinnamic acids, for example, chlorogenic acid, verbascoside; phenolic aldehydes; phenylpropenes; coumarins, coumestans, or tyrosols, as well as combinations thereof.

In one embodiment, the polyphenols may be plant-based and/or organic.

In certain exemplary embodiments, polyphenols useful according to the disclosure may be chosen from tannic acid, resveratrol, catechin, ellagic acid, resorcinol, gallic acid, humic acid, chlorogenic acid, quercetin, anthocyanin, chebulinic acid or mixtures thereof. In one exemplary embodiment, the polyphenol is tannic acid.

The total amount of the at least one polyphenol may vary, but typically ranges from about 0.01% to about 20%, about 0.1% to about 15%, about 1% to about 10%, or about 1% to about 5%, based on the total weight of the composition. For example, the total amount of the at least one polyphenol may range from about 0.01% to about 10%, such as from about 0.01% to about 9%, about 0.01% to about 8%, about 0.01% to about 7%, about 0.01% to about 6%, about 0.01% to about 5%, about 0.01% to about 4%, about 0.01% to about 3%, about 0.01% to about 2%, about 0.01% to about 1%, about 0.01% to about 0.75%, about 0.01% to about 0.5%, about 0.05% to about 10%, about 0.05% to about 9%, about 0.05% to about 8%, about 0.05% to about 7%, about 0.05% to about 6%, about 0.05% to about 5%, about 0.05% to about 4%, about 0.05% to about 3%, about 0.05% to about 2%, about 0.05% to about 1%, about 0.05% to about 0.75%, about 0.05% to about 0.5%, about 0.1% to about 10%, about 0.1% to about 9%, about 0.1% to about 8%, about 0.1% to about 7%, about 0.1% to about 6%, about 0.1% to about 5%, about 0.1% to about 4%, about 0.1% to about 3%, about 0.1% to about 2%, about 0.1% to about 1%, about 0.1% to about 0.75%, about 0.1% to about 0.5%, about 0.5% to about 10%, about 0.5% to about 9%, about 0.5% to about 8%, about 0.5% to about 7%, about 0.5% to about 6%, about 0.5% to about 5%, about 0.5% to about 4%, about 0.5% to about 3%, about 0.5% to about 2%, about 0.5% to about 1%, about 1% to about 10%, about 1% to about 9%, about 1% to about 8%, about 1% to about 7%, about 1% to about 6%, about 1% to about 5%, about 1% to about 4%, about 1% to about 3%, about 1% to about 2%, about 2% to about 10%, about 2% to about 9%, about 2% to about 8%, about 2% to about 7%, about 2% to about 6%, about 2% to about 5%, about 2% to about 4%, about 2% to about 3%, about 3% to about 10%, about 3% to about 9%, about 3% to about 8%, about 3% to about 7%, about 3% to about 6%, about 3% to about 5%, about 3% to about 4%, about 4% to about 10%, about 4% to about 9%, about 4% to about 8%, about 4% to about 7%, about 4% to about 6%, about 4% to about 5%, about 5% to about 10%, about 5% to about 9%, about 5% to about 8%, about 5% to about 7%, or about 5% to about 6%, including all ranges and sub-ranges there between, based on the total weight of the composition.

In various embodiments, the at least one polyphenol may be present in an amount of about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, or about 10%, based on the total weight of the composition.

Polymers

The compositions described herein optionally comprise at least one film forming or fixing polymer. As used herein, the terms "film forming polymer" or "fixing polymer" are understood to mean any polymer that is capable, when applied to the eyelashes, of forming a film on eyelashed, thereby allowing the hair to retain a desired shape. Without wishing to be bound by theory, it is believed that the polyphenol may act as a crosslinker to the polymer, which unexpectedly results in synergistically improved eyelash curling properties.

Useful film forming polymers include synthetic, semi-synthetic, or natural and/or plant-based and/or organic polymers. Any anionic, cationic, amphoteric, and non-ionic film forming polymers, as well as mixtures thereof, may be used in the disclosed compositions and methods.

By way of non-limiting example, anionic film forming polymers that can be used in the disclosed compositions are polymers comprising groups derived from carboxylic acid, sulfonic acid or phosphoric acid and have a number-average molecular weight of ranging from approximately 500 and 5,000,000.

The carboxylic groups are provided by unsaturated monocarboxylic or dicarboxylic acid monomers such as those corresponding to the formula (II):

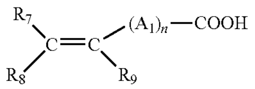

in which n is an integer from 0 to 10, $A_1$ denotes a methylene group optionally joined to the carbon atom of the unsaturated group or to the adjacent methylene group when n is greater than 1, via a heteroatom such as oxygen or sulfur, $R_7$ denotes a hydrogen atom or a phenyl or benzyl group, $R_3$ denotes a hydrogen atom or a lower alkyl or carboxyl group, and $R_9$ denotes a hydrogen atom, a lower alkyl group, or a $CH_2$—COOH, phenyl or benzyl group.

In the abovementioned formula, a lower alkyl group may denote a group having 1 to 4 carbon atoms, and in particular the methyl and ethyl groups.

By way of non-limiting example, anionic film forming polymers comprising carboxylic groups which may be used in the disclosed compositions are:

A) copolymers of acrylic or methacrylic acid or salts thereof. Among these polymers, mention may be made of copolymers of acrylic or methacrylic acid with a monoethylenic monomer such as ethylene, styrene, vinyl esters, acrylic or methacrylic acid esters, optionally grafted onto a polyalkylene glycol such as polyethylene glycol and optionally crosslinked. Such polymers are described in particular in French patent No. 1 222 944 and German patent application No. 2 330 956, the copolymers of this type comprising an optionally N-alkylated and/or hydroxyalkylated acrylamide unit in their chain as described in particular in Luxembourg patent application Nos. 75370 and 75371. Mention may also be made of copolymers of acrylic acid and of $C_1$-$C_4$ alkyl methacrylate and terpolymers of vinylpyrrolidone, of acrylic acid and of $C_1$-$C_{20}$ alkyl methacrylate, for example lauryl methacrylate, such as the product sold by the company ISP under the name Acrylidone® LM (INCI name VP/acrylates/lauryl methacrylate copolymer), acrylic acid/ethyl acrylate/N-t-butylacrylamide terpolymers, such as the products Ultrahold® Strong and Ultrahold® 8 sold by the company BASF (INCI name Acrylates/t-butylacrylamide copolymer), methacrylic acid/ethyl acrylate/tert-butyl acrylate terpolymers, such as the products sold under the names Luvimer® 100 P or Luvimer® PRO 55 by the company BASF (INCI name Acrylates copolymer), copolymers of methacrylic acid and of ethyl acrylate, such as the products sold under the names Luvimer® MAE or Luviflex® Soft by the company BASF (INCI name Acrylates copolymer), acrylic acid/butyl acrylate/methyl methacrylate terpolymers, such as the product sold under the name Balance® CR by the company Akzo Nobel (INCI name Acrylates copolymer), and the copolymers of methacrylic acid and of methyl methacrylate sold under the name Eudragit® L 100 by the company Rohm Pharma (INCI name Acrylates copolymer). Mention may also be made of branched block polymers containing (meth)acrylic acid monomers, such as the product sold under the name Fixate® G-100L by the company Lubrizol (INCI name AMP-acrylates/allyl methacrylate copolymer);

B) crotonic acid copolymers, such as those comprising vinyl acetate or propionate units in their chain and optionally other monomers such as allyl esters or methallyl esters, vinyl ether or vinyl ester of a linear or branched saturated carboxylic acid with a long hydrocarbon-based chain, such as those containing at least 5 carbon atoms, it being possible for these polymers optionally to be grafted or crosslinked, or alternatively another vinyl, allyl or methallyl ester monomer of an α- or β-cyclic carboxylic acid. Such polymers are described, inter alia, in French patent Nos. 1 222 944, 1 580 545, 2 265 782, 2 265 781, 1 564 110 and 2 439 798. Commercial products which fall into this category are the products Resyn® 28-2930 and 28-1310 sold by the company Akzo Nobel (INCI names VA/crotonates/vinyl decanoate copolymer and VA/crotonates copolymer, respectively). Mention may also be made of the products Luviset® CA 66 sold by the company BASF, Aristoflex® A60 sold by the company Clariant (INCI name VA/crotonates copolymer) and Mexomere® PW or PAM sold by the company Chimex (INCI name VA/vinyl butyl benzoate/crotonates copolymer);

C) copolymers of monounsaturated $C_4$-$C_8$ carboxylic acids or anhydrides selected from:

copolymers comprising (i) one or more maleic, fumaric or itaconic acids or anhydrides and (ii) at least one monomer chosen from vinyl esters, vinyl ethers, vinyl halides, phenylvinyl derivatives, acrylic acid and its esters, the anhydride functions of these copolymers optionally being monoesterified or monoamidated. Such polymers are described, in particular, in U.S. Pat. Nos. 2,047,398, 2,723,248 and 2,102,113, and GB patent No. 839 805. By way of non-limiting example, maleic acid/anhydride copolymers that may be useful include methyl vinyl ether-maleic acid copolymer, such as that available commercially from ISP under the tradename GANTREZ® S (e.g., GANTREZ® S-97 BF; INCI name PVM/MA copolymer), methyl vinyl ether-maleic anhydride copolymer, such as that available commercially from ISP under the tradename GANTREZ® AN (INCI name polymethylvinylether/maleic anhydride copolymer), isobutyl vinyl ether-maleic anhydride copolymer, ethylene-maleic anhydride copolymer, isobutylene-maleic anhydride copolymer, styrene-maleic anhydride copolymer, vinyltriazole-maleic anhydride copolymer and vinylnorbornene-maleic anhydride copolymer. The copolymers may contain, in addition to the at least one copolymerizable monomer, both maleic acid and maleic anhydride, or a derivative thereof. Additional useful commercial products include those sold under the names Gantrez® ES by the company ISP, such as Gantrez® ES 225 (INCI name ethyl ester of PVM/MA copolymer) or Gantrez® ES 425L (INCI name butyl ester of PVM/MA copolymer). In an embodiment, the disclosed polymer may be Gantrez® PVM/MA (Poly(methyl vinyl ether-alt-maleic acid)(CAS Number 25153-40-6). The PVM/MA copolymer, or Poly(methyl vinyl ether-alt-maleic acid, may have an average Mw of approximately 1,980,000 by LS, and/or an average Mn of approximately 960,000 (powder). For example, the molecular weight of PVM/MA may be from about 75,000 to about 3,000,000 g/mol, about 150,000 to about 2,750,000 g/mol, about 300,000 to about 2,500,000 g/mol, about 450,000 to about 2,250,000 g/mol, about 600,000 to 2,200,000 about g/mol, about 850,000 to 2,150,000 about g/mol, about 1,100,000 to 2,100,000 about g/mol, about 1,225,000 to 2,005,000 about g/mol, about 1,500,000 and about 2,000,000 g/mol about 1,650,000 to 1,850,000 about g/mol. The PVM/MA (Poly(methyl vinyl ether-alt-maleic acid) may have a formula of formula (I):

$$[CH_2CH(OCH_3)CH(CO_2H)CH(CO_2H)]n \quad (I)$$

wherein n is a number from about 2,500 to about 17,500, from about 3,000 to about 17,000, from about 3,500 to about 16,500, from about 4,000 to about 16,000, from about 4,500 to about 15,500, from about 5,000 to about 15,000, from about 5,500 to about 14,500, from about 6,000 to about 14,000, from about 6,500 to about 13,500, from about 7,000 to about 13,000, from about 7,500 to about 12,500, from about 8,000 to about 12,000, from about 8,500 to about 11,500, from about 9,000 to about 11,000, or from about 9,500 to about 10,500.

copolymers comprising (i) one or more maleic, citraconic or itaconic anhydride units and (ii) one or more monomers chosen from allyl or methallyl esters optionally comprising one or more acrylamide, methacrylamide, α-olefin, acrylic or methacrylic ester, acrylic or methacrylic acid or vinylpyrrolidone groups in their chain, the anhydride functions of these copolymers optionally being monoesterified or monoamidated. These polymers are described, for example, in French patent Nos. 2 350 384 and 2 357 241;

D) polyacrylamides comprising carboxylate groups. The film forming polymers comprising units derived from sulfonic acid can be chosen from:

A') homopolymers and copolymers comprising vinylsulfonic, styrenesulfonic, naphthalenesulfonic or acrylamidoalkylsulfonic units.

These polymers can be chosen in particular from:

polyvinylsulfonic acid salts having a molecular weight of approximately ranging from 1000 and 100,000, and also the copolymers with an unsaturated comonomer such as acrylic or methacrylic acids and their esters, and also acrylamide or its derivatives, vinyl ethers and vinylpyrrolidone;

polystyrenesulfonic acid salts such as the sodium salts that are sold for example under the name Flexan® II by Akzo Nobel (INCI name Sodium polystyrene sulfonate). These compounds are described in patent FR 2 198 719;

polyacrylamidosulfonic acid salts, such as those mentioned in U.S. Pat. No. 4,128,631, and more particularly the polyacrylamidoethylpropanesulfonic acid, sold under the name Rheocare® HSP-1180 by Cognis (INCI name polyacrylamidomethyl-propane sulfonic acid);

B') sulfonic polyesters, these polymers being obtained by polycondensation of at least one dicarboxylic acid, of at least one diol or of a mixture of diol and of diamine, and of at least one difunctional monomer comprising a sulfonic function. Among these polymers, mention may be made of:

linear sulfonic polyesters such as those described in U.S. Pat. Nos. 3,734,874, 3,779,993, 4,119,680, 4,300,580, 4,973,656, 5,660,816, 5,662,893 and 5,674,479. Such polymers are, for example, the products Eastman® AQ38S Polymer, Eastman® AQ55S Polymer and Eastman® AQ48 Ultra Polymer sold by the company Eastman Chemical (name Polyester-5) which are copolymers obtained from diethylene glycol, from 1,4-cyclohexanedimethanol, from isophthalic acid and from sulfoisophthalic acid salt;

branched sulfonic polyesters such as those described in patent applications WO 95/18191, WO 97/08261 and WO 97/20899. Such compounds are, for example, the products Eastman® AQ10D Polymer (name Polyester-13) or Eastman® AQ1350 Polymer provided by the company Eastman Chemical (name Polyester-13).

In an embodiment, the anionic film forming polymers are chosen from copolymers of acrylic acid, such as the acrylic acid/ethyl acrylate/N-tert-butylacrylamide terpolymers sold in particular under the name Ultrahold® Strong by the company BASF, copolymers derived from crotonic acid, such as vinyl acetate/vinyl tert-butylbenzoate/crotonic acid terpolymers and the crotonic acid/vinyl acetate/vinyl neododecanoate terpolymers sold in particular under the name Resyn 28-2930 by the company Akzo Nobel, polymers derived from maleic, fumaric or itaconic acids or anhydrides with vinyl esters, vinyl ethers, vinyl halides, phenylvinyl derivatives and acrylic acid and esters thereof, such as the methyl vinyl ether/monoesterified maleic anhydride copolymers sold, for example, under the names Gantrez® ES 425L or ES 225 by the company ISP, the copolymers of methacrylic acid and of ethyl acrylate sold under the name Luvimer® MAE by the company BASF, and the vinyl acetate/crotonic acid copolymers sold under the name Luviset® CA 66 by the company BASF, and the vinyl acetate/crotonic acid copolymers grafted with polyethylene glycol sold under the name Aristoflex® A60 by the company Clariant, the vinylpyrrolidone/acrylic acid/lauryl methacrylate terpolymers sold under the name Acrylidone® LM by the company ISP, the polymer sold under the name Fixate® G-100L by the company Lubrizol, the vinyl acetate/crotonic acid/vinyl p-tert-butylbenzoate copolymers sold under the names Mexomere® PW or PAM by the company Chimex.

By way of non-limiting example, the cationic film forming film-forming polymers that can be used in the disclosed composition may be chosen from polymers comprising primary, secondary, tertiary and/or quaternary amine groups forming part of the polymer chain or directly attached thereto, and having a molecular weight of ranging from 500 and about 5,000,000 and preferably ranging from 1000 and 3,000,000.

Among these polymers, mention may be made more particularly of the following cationic polymers:

(1) homopolymers or copolymers derived from acrylic or methacrylic esters or amides and comprising at least one of the units of the following formulae:

(A)

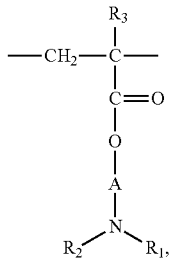

(B)

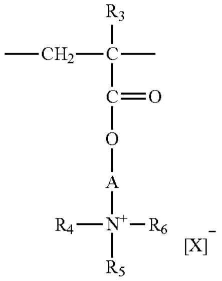

ou (C)

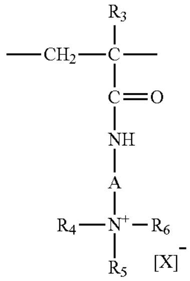

(D)

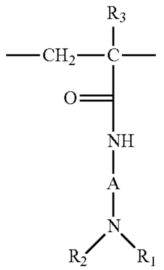

in which:

$R_3$ denotes a hydrogen atom or a $CH_3$ radical;

A is a linear or branched alkyl group comprising from 1 to 6 carbon atoms or a hydroxyalkyl group comprising from 1 to 4 carbon atoms;

$R_4$, $R_5$ and $R_6$, which may be identical or different, represent an alkyl group having from 1 to 18 carbon atoms or a benzyl radical;

$R_1$ and $R_2$, which may be identical or different, each represent a hydrogen atom or an alkyl group having from 1 to 6 carbon atoms;

X denotes a methosulfate anion or a halide such as chloride or bromide.

The copolymers of family (1) also contain one or more units derived from comonomers that may be chosen from the family of acrylamides, methacrylamides, diacetone acrylamides, acrylamides and methacrylamides substituted on the nitrogen with lower ($C_1$-$C_4$) alkyl groups, groups derived from acrylic or methacrylic acids or esters thereof, vinyllactams such as vinylpyrrolidone or vinylcaprolactam, and vinyl esters.

Thus, among these copolymers of family (1), mention may be made of:

quaternized or non-quaternized vinylpyrrolidone/dialkylaminoalkyl acrylate or methacrylate copolymers, such as the products sold under the name Gafquat® by the company ISP, for instance Gafquat® 734 or Gafquat® 755 or Gafquat® 755N (INCI name Polyquaternium-11), or alternatively the products known as Copolymer® 845, 958 and 937 sold by ISP (INCI name VP/dimethylaminoethyl methacrylate copolymer). These polymers are described in detail in French patents 2 077 143 and 2 393 573, fatty-chain polymers containing a vinylpyrrolidone unit, such as the products sold under the name Styleze® W20L and Styleze® W10 by the company ISP (INCI name Polyquaternium-55), dimethylaminoethyl methacrylate/vinylcaprolactam/vinylpyrrolidone terpolymers, such as the products sold under the names Advantage HC 37 or Gaffix® VC 713 by the company ISP (INCI name Vinyl caprolactam/VP/dimethylaminoethyl methacrylate copolymer), and quaternized vinylpyrrolidone/dimethylaminopropylmethacrylamide copolymers, such as the products sold under the name Gafquat® HS 100 by the company ISP (name Polyquaternium-28);

(2) cationic guar gum derivatives, preferably containing quaternary ammonium, such as those described in U.S. Pat. Nos. 3,589,578 and 4,031,307, such as guar gums containing trialkylammonium cationic groups. Such products are sold in particular under the trade names Jaguar® C13 S, Jaguar® C 15 and Jaguar® C 17 by the company Rhodia (INCI name Guar hydroxypropyltrimonium chloride);

(3) quaternary copolymers of vinylpyrrolidone and of vinylimidazole; mention may be made, for example, of vinylpyrrolidone/methylvinylimidazolium chloride copolymers, such as the products sold by the company BASF under the names Luviquat® FC550 or FC370, Luviquat® Excellence and Luviquat® Style (INCI name Polyquaternium-16), or vinylpyrrolidone/vinylimidazolium methosulfate/vinylcaprolactam terpolymers, such as the product Luviquat® Hold sold by the company BASF (INCI name Polyquaternium-46);

(4) chitosans or salts thereof; the salts that can be used are, in particular, chitosan acetate, lactate, glutamate, gluconate or pyrrolidonecarboxylate. Among these compounds, mention may be made of the chitosan pyrrolidonecarboxylate sold under the name Kytamer® PC by the company Amerchol (INCI name Chitosan PCA);

(5) cationic cellulose derivatives such as copolymers of cellulose or of cellulose derivatives grafted with a water-soluble monomer comprising a quaternary ammonium, and described in particular in U.S. Pat. No. 4,131,576, such as hydroxyalkylcelluloses, for instance hydroxymethyl-, hydroxyethyl- or hydroxypropylcelluloses grafted in particular with a methacryloyloxyethyltrimethylammonium, methacrylamidopropyltrimethyl-ammonium or dimethyldiallylammonium salt. The commercial products corresponding to this definition are, more particularly, the products sold under the name Celquat® L 200 and Celquat® H 100 by the company Akzo Nobel (INCI name Polyquaternium-4).

The amphoteric film forming polymers that may be used in accordance with the invention may be selected from polymers comprising units B and C distributed statistically in the polymer chain, where B denotes a unit derived from a monomer comprising at least one basic nitrogen atom and C denotes a unit derived from an acid monomer comprising one or more carboxylic or sulfonic groups, or alternatively B and C may denote groups derived from carboxybetaine or sulfobetaine zwitterionic monomers;

Additionally, B and C can also denote a cationic polymer chain comprising primary, secondary, tertiary or quaternary amine groups, in which at least one of the amine groups bears a carboxylic or sulfonic group connected via a hydrocarbon-based group, or alternatively B and C form part of a chain of a polymer comprising an $\alpha,\beta$-dicarboxylic ethylene unit in which one of the carboxylic groups has been made to react with a polyamine comprising one or more primary or secondary amine groups.

The amphoteric film forming polymers corresponding to the definition given above may be chosen from the following polymers:

(1) copolymers containing acidic vinyl units and basic vinyl units, such as those resulting from the copolymerization of a monomer derived from a vinyl compound bearing a carboxylic group such as, more particularly, acrylic acid, methacrylic acid, maleic acid, $\alpha$-chloroacrylic acid, and of a basic monomer derived from a substituted vinyl compound containing at least one basic atom, such as, more particularly, dialkylaminoalkyl methacrylate and acrylate, dialkylaminoalkylmethacrylamide and acrylamide. Such compounds are described in U.S. Pat. No. 3,836,537;

(2) polymers comprising units deriving from:

a) at least one monomer chosen from acrylamides or methacrylamides substituted on the nitrogen atom with an alkyl group, b) at least one acidic comonomer containing one or more reactive carboxylic groups, and c) at least one basic comonomer such as esters containing primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides may be chosen from compounds in which the alkyl groups contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers may be chosen from acrylic, methacrylic, crotonic, itaconic, maleic and fumaric acid and also alkyl monoesters, having 1 to 4 carbon atoms, of maleic or fumaric acid or anhydride. The basic comonomers may be chosen from aminoethyl, butylaminoethyl, N,N'-dimethylaminoethyl and N-tert-butylaminoethyl methacrylates.

The copolymers of which the INCI name is octylacrylamide/acrylates/butylaminoethyl methacrylate copolymer, such as the products sold under the names Amphomer®, Amphomer® LV71 or Balance® 47 by the company Akzo Nobel, may be used;

(3) crosslinked and acylated polyaminoamides partially or totally deriving from polyaminoamides of general formula (III):

$$-[CO-R_{10}-CO-Z]- \qquad \text{(III)}$$

in which:

$R_{10}$ represents a divalent group derived from a saturated dicarboxylic acid, a mono- or dicarboxylic aliphatic acid containing an ethylenic double bond, an ester of a lower alkanol having 1 to 6 carbon atoms of these acids, or a group derived from the addition of any one of said acids to a bis(primary) or bis(secondary) amine, and Z denotes a group derived from a bis(primary), mono (secondary) or bis(secondary) polyalkylene-polyamine and may represent:

a) in proportions of from 60 to 100 mol %, the group of formula:

$$-NH-[(CH_2)_x-NH]_p- \qquad \text{(IV)}$$

where x=2 and p=2 or 3, or alternatively x=3 and p=2, this group deriving from diethylenetriamine, from triethylenetetramine or from dipropylenetriamine;

b) in proportions of from 0 to 40 mol %, the group (IV) above in which x=2 and p=1 and which is derived from ethylenediamine, or the group deriving from piperazine for formula (V):

(V)

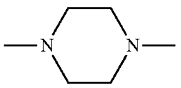

c) in proportions of from 0 to 20 mol %, the group —NH—$(CH_2)$s-NH— deriving from hexamethylenediamine, these polyaminoamides being crosslinked by addition reaction of a difunctional crosslinking agent chosen from epihalohydrins, diepoxides, dianhydrides and bis-unsaturated derivatives, using from 0.025 to 0.35 mol of crosslinking agent per amine group of the polyaminoamide and acylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid and 2,4,4-trimethyladipic acid, terephthalic acid, acids containing an ethylenic double bond such as, for example, acrylic acid, methacrylic acid and itaconic acid.

The alkane sultones used in the acylation may be propane sultone or butane sultone; the salts of the acylating agents may be the sodium or potassium salts;

(4) polymers comprising zwitterionic units of formula (VI):

(VI)

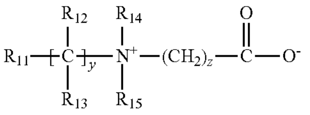

in which:

$R_{11}$ denotes a polymerizable unsaturated group such as an acrylate, methacrylate, acrylamide or methacrylamide group, y and z represent an integer from 1 to 3, $R_{12}$ and $R_{13}$ represent a hydrogen atom, or a methyl, ethyl or propyl group, and $R_{14}$ and $R_{15}$ represent a hydrogen atom or an alkyl group such that the sum of the carbon atoms in $R_{14}$ and $R_{15}$ does not exceed 10.

The polymers comprising such units may also comprise units derived from non-zwitterionic monomers such as dimethyl- or diethylaminoethyl acrylate or methacrylate or alkyl acrylates or methacrylates, acrylamides or methacrylamides or vinyl acetate. Mention may be made, by way of example, of methyl methacrylate/methyl dimethylcarboxymethylammonioethyl methacrylate copolymers, such as the product sold under the name Diaformer Z-301N or Z-301W by the company Clariant (INCI name Acrylates copolymer);

(5) polymers derived from chitosan comprising monomer units corresponding to the following formula:

(D)

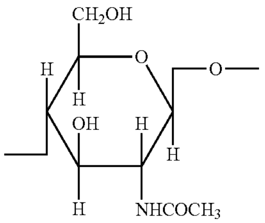

(E)

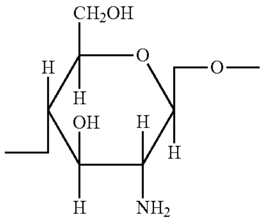

(F)

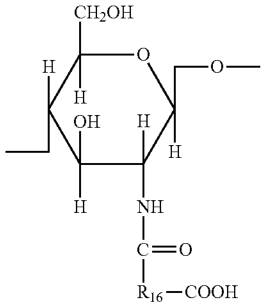

wherein:

the unit (D) is present in proportions ranging from 0% to 30%, the unit (E) is present in proportions ranging from 5% to 50%, and the unit (F) is present in proportions ranging from 30% to 90%, it being understood that, in this unit (F), $R_{16}$ represents a group of formula (VII):

(VII)

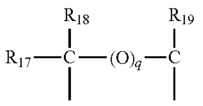

in which, if q=0, then $R_{17}$, $R_{13}$ and $R_{19}$, which may be identical or different, each represent a hydrogen atom, a methyl, hydroxyl, acetoxy or amino residue, a monoalkylamine residue or a dialkylamine residue that are optionally interspersed with one or more nitrogen atoms and/or optionally substituted with one or more amine, hydroxyl, carboxyl, alkylthio or sulfonic groups, or an alkylthio residue in which the alkyl group bears an amino residue, at least one of the groups $R_{17}$, $R_{13}$ and $R_{19}$ being, in this case, a hydrogen atom; or, if q=1, then $R_{17}$, $R_{13}$ and $R_{19}$ each represent a hydrogen atom, and also the salts formed by these compounds with bases or acids;

(6) polymers containing units corresponding to general formula (VIII) are described, for example, in French patent 1 400 366:

(VIII)

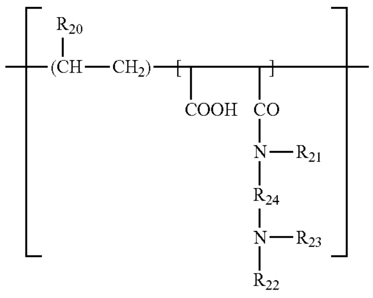

in which:

$R_{20}$ represents a hydrogen atom, a $CH_3O$, $CH_3CH_2O$ or phenyl group, $R_{21}$ denotes a hydrogen atom or a lower alkyl group such as methyl or ethyl, $R_{22}$ denotes a hydrogen atom or a $C_1$-$C_6$ lower alkyl group such as methyl or ethyl, $R_{24}$ representing a group $—CH_2—CH_2—$, $—CH_2—CH_2—CH_2—$ or $—CH_2—CH(CH_3)—$, and $R_{23}$ denotes a $C_1$-$C_6$ lower alkyl group such as methyl or ethyl or a group corresponding to the formula (IX):

$$—R_{24}—N(R_{22})_2 \quad \text{(IX)}$$

with $R_{22}$ and $R_{24}$ having the meanings mentioned above;

(7) polymers derived from the N-carboxyalkylation of chitosan, such as N-carboxymethyl chitosan or N-carboxybutyl chitosan, for instance the product sold under the name Chitoglycan by the company Sinerga SPA (INCI name Carboxymethyl chitosan);

(8) amphoteric polymers of the -D-X-D-X type chosen from:

a) polymers obtained by the action of chloroacetic acid or sodium chloroacetate on compounds comprising at least one unit of formula (X):

-D-X-D-X-D- (X)

where D denotes a group of formula (XI)

(XI)

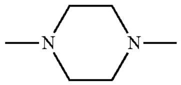

and X denotes the symbol E or E', E or E', which may be identical or different, denote a divalent group that is an alkylene group with a straight or branched chain containing up to 7 carbon atoms in the main chain, which is unsubstituted or substituted with hydroxyl groups and which can comprise, in addition to the oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;

b) polymers of formula (XII):

-D-X-D-X— (XII)

where D denotes a group of formula (XIII)

(XIII)

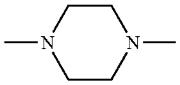

and X denotes the symbol E or E' and at least once E'; E having the meaning given above and E' is a divalent group that is an alkylene group with a straight or branched chain having up to 7 carbon atoms in the main chain, which is unsubstituted or substituted with one or more hydroxyl groups and containing one or more nitrogen atoms, the nitrogen atom being substituted with an alkyl chain that is optionally interrupted by an oxygen atom and necessarily comprising one or more carboxyl functions or one or more hydroxyl functions and betainized by reaction with chloroacetic acid or sodium chloroacetate;

(9) ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkylaminoalkanol. These copolymers can also comprise other vinyl comonomers such as vinylcaprolactam.

Among the amphoteric film forming polymers mentioned above that are most particularly preferred according to the invention, mention will be made of those of family (3), such as the copolymers of which the INCI name is Octylacrylamide/acrylates/butylaminoethyl methacrylate copolymer, such as the products sold under the names Amphomer®, Amphomer® LV 71 or Balance® 47 by the company Akzo Nobel and those of family (4), such as the methyl methacrylate/methyl dimethylcarboxymethyl-ammonioethyl methacrylate copolymers sold, for example, under the name Diaformer Z-301N or Z-301W by the company Clariant.

The non-ionic film forming polymers that may be used according to the present invention may be chosen, for example, from:

polyalkyloxazolines;

vinyl acetate homopolymers;

vinyl acetate copolymers, for instance copolymers of vinyl acetate and of acrylic ester; copolymers of vinyl acetate and of ethylene, or copolymers of vinyl acetate and of maleic ester, for example of dibutyl maleate;

homopolymers and copolymers of acrylic esters, for instance copolymers of alkyl acrylates and of alkyl methacrylates, such as the products provided by the company Rohm GmbH under the name Eudragit® NE 30 D (INCI name Acrylates copolymer);

copolymers of acrylonitrile and of a non-ionic monomer, chosen, for example, from butadiene and alkyl (meth) acrylates;

styrene homopolymers;

styrene copolymers, for instance copolymers of styrene, of alkyl acrylate and of alkyl methacrylate; copolymers of styrene and of butadiene, or copolymers of styrene, of butadiene and of vinylpyridine;

polyamides;

vinyllactam homopolymers, such as the vinylpyrrolidone homopolymers sold, for example, under the names Luviskol® K30 powder by the company BASF or PVP K30L or K60 solution or K90 by the company ISP, or such as the polyvinylcaprolactam sold under the name Luviskol® Plus by the company BASF (INCI name PVP);

vinyllactam copolymers, such as a poly(vinylpyrrolidone/vinyllactam) copolymer sold under the trade name Luvitec® VPC 55K65W by the company BASF, poly (vinylpyrrolidone/vinyl acetate) copolymers, such as those sold under the name PVP/VA® S630L, E735, E635 and W735 by the company ISP, Luviskol® VA 73, VA 64 and VA 37 by the company BASF (INCI name VP/VA copolymer); and vinylpyrrolidone/methacrylamide/vinylimidazole terpolymers, for instance the product sold under the name Luviset® Clear by the company BASF (INCI name VP/methacrylamide/vinyl imidazole copolymer).

The alkyl groups of the abovementioned non-ionic polymers may have from 1 to 6 carbon atoms.

In certain exemplary embodiments, it is also possible to use film forming polymers of grafted silicone type comprising a polysiloxane portion and a portion constituted of a non-silicone organic chain, one of the two portions constituting the main chain of the polymer and the other being grafted to the main chain.

These polymers are described, for example, in patent applications EP-A-0 412 704, EP-A-0 412 707, EP-A-0 640 105 and WO 95/00578, EP-A-0 582 152 and WO 93/23009 and U.S. Pat. Nos. 4,693,935, 4,728,571 and 4,972,037.

These polymers may be amphoteric, anionic or non-ionic.

Such polymers are, for example, copolymers that may be obtained by free radical polymerization from the monomer mixture formed:

a) of 50% to 90% by weight of tert-butyl acrylate, b) of 0% to 40% by weight of acrylic acid, c) of 5% to 40% by weight of a silicone macromer of formula (XIX):

(XIX)

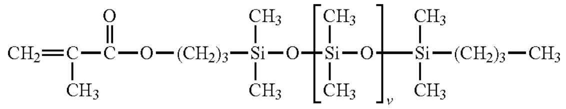

in which v is a number ranging from 5 to 700, the weight percentages being calculated relative to the total weight of the monomers.

Other examples of grafted silicone polymers include polydimethylsiloxanes (PDMSs) to which mixed polymer units of the poly(meth)acrylic acid type and of the poly(alkyl (meth)acrylate) type are grafted via a thiopropylene-type connecting link and polydimethylsiloxanes (PDMSs) to which polymer units of the poly(isobutyl (meth)acrylate) type are grafted via a thiopropylene-type connecting link.

Grafted silicone polymers are, for example, sold under the names Silicone Plus Polymer® VS80 and VA70 by 3M (INCI names Polysilicone-8 and Polysilicone-7 respectively).

Another type of silicone film forming polymer that may be mentioned is the product Luviflex® Silk sold by BASF (INCI name PEG/PPG-25/25 dimethicone/acrylates Copolymer).

As film forming polymers, it is also possible to use functionalized or non-functionalized, cationic, non-ionic, anionic or amphoteric, silicone or non-silicone polyurethanes, or mixtures thereof.

The polyurethanes that may be used in the disclosed compositions are those described in patent applications EP 0 751 162, EP 0 637 600, EP 0 648 485 and FR 2 743 297, and patent applications EP 0 656 021 and WO 94/03510 from the company BASF and EP 0 619 111 from the company National Starch.

Mention may be made, as polyurethanes suitable in the present invention, of the products sold under the names Luviset PUR® and Luviset® Si PUR by the company BASF (INCI names Polyurethane-1 and Polyurethane-6 respectively).

As yet further non-limiting examples, polymers useful according to the disclosure may be chosen from polysaccharides. Non-limiting examples of polysaccharides include oxidized inulins, celluloses, starches, guar gums, xanthan gums, pullulan gums, alginate gums, agar-agar gums, carrageenan gums, gellan gums, chitosan, gums arabic, xyloses and tragacanth gums, and derivatives thereof, cellobiose, maltodextrin, scleroglucan, chitosan, ulvan, fucoidan, alginate, pectin, heparin and hyaluronic acid, or mixtures thereof.

In certain exemplary embodiments, polysaccharides useful according to the disclosure may be chosen from gums. Non-limiting examples of gums include acacia, agar, algin, alginic acid, ammonium alginate, amylopectin, calcium alginate, calcium carrageenan, carrageenan, dextrin, gelatin, gellan gum, guar gum, gum Arabic, hydroxypropyl guar, guar hydroxypropyltrimonium chloride, hydroxypropyl guar hydroxypropyltrimonium chloride, karaya gum, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

Further non-limiting examples of polymers useful according to the disclosure include non-cellulose cationic polysaccharides, such as guar gums containing trialkylammonium cationic groups. Suitable cationic guar gum derivatives include those given the PCPC (Personal Care Products Council, formerly CTFA, designation) of guar hydroxypropyl trimonium chloride, available commercially for example as JAGUAR C13S. Other suitable materials include that known as JAGUAR C15, JAGUAR C17, and JAGUAR C16 which is a hydroxypropylated cationic guar derivative containing a low level of substituent groups as well as cationic quaternary ammonium groups. Guar hydroxypropyl trimonium chloride, may also be available commercially for example as N-HANCE CG13 from the company Ashland. Also suitable is hydroxypropyl guar hydroxypropyltrimonium chloride, commercially available as JAGUAR 162.

In an exemplary embodiment, the at least one film forming polymer may be chosen from acrylate-based polymers, polyurethanes, and polysaccharides or mixtures thereof. In a further exemplary embodiment, the polymer may be chosen from PVM/MA (Poly(methyl vinyl ether-alt-maleic acid) (e.g. sold under the name Gantrez®), carrageenan, gum Arabic, oxidized inulin, alginate, xanthan gum, xylan, chitosan, or mixtures thereof. In yet a further exemplary embodiment, the polymer may be PVM/MA (Poly(methyl vinyl ether-alt-maleic acid) (e.g. sold under the name Gantrez®), carrageenan, or mixtures thereof.

The total amount of the at least one film forming polymer may vary, but typically ranges from about 0.001% to about 10%, such as from about 0.01% to about 5%, about 0.05% to about 3%, about 0.1% to about 2%, or about 0.5% to about 1%, based on the total weight of the composition. For example, the total amount of the film forming polymer may range from about 0.01% to about 10%, about 0.01% to about 9%, about 0.01% to about 8%, about 0.01% to about 7%, about 0.01% to about 6%, about 0.01% to about 5%, about 0.01% to about 4%, about 0.01% to about 3%, about 0.01% to about 2%, about 0.01% to about 1%, about 0.1% to about 10%, about 0.1% to about 9%, about 0.1% to about 8%, about 0.1% to about 7%, about 0.1% to about 6%, about 0.1% to about 5%, about 0.1% to about 4%, about 0.1% to about 3%, about 0.1% to about 2%, about 0.1% to about 1%, about 0.5% to about 10%, about 0.5% to about 9%, about 0.5% to about 8%, about 0.5% to about 7%, about 0.5% to about 6%, about 0.5% to about 5%, about 0.5% to about 4%, about 0.5% to about 3%, about 0.5% to about 2%, about 0.5% to about 1.5%, or about 0.5% to about 1%, including all ranges and sub-ranges there between, based on the total weight of the composition. In certain embodiments, the at least one film forming polymer may be present in an amount of about 0.05%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, or about 2%, based on the total weight of the composition.

Optionally, the weight ratio of the total amount of polyphenol to the film-forming polymer may be chosen to range from about 1:100 to about 100:1, about 1:30 to about 30:1, such as about 1:10 to about 10:1, or about 1:4 to about 4:1, about 1:3 to about 3:1, or about 1:2 to about 2:1. In some embodiments, the weight ratio of the total amount of polyphenol to the film-forming polymer is greater than 1, for example ranges from about 1 to about 50, about 1 to about 25, about 1 to about 10, or about 5 to about 10. For example, the weight ratio of the total amount of polyphenol to the film-forming polymer may be about 5, about 10, about 25, or about 50.

In at least certain embodiments, the compositions are free or substantially free of film forming polymers.

In some embodiments, the compositions are free or substantially free of synthetic gums, silicones, and/or synthetic polymers. For example, the compositions may include less than about 3%, less than about 2%, less than about 1%, or less than about 0.5% of synthetic gums, silicones, and/or synthetic polymers, and in some embodiments comprise no synthetic gums, silicones, and/or synthetic polymers. In some embodiments, however, the compositions may comprise synthetic gums, silicones, and/or synthetic polymers. Non-limiting examples of silicones include amine-functionalized silicones (e.g., amodimethicone), dimethicone, bis-aminopropyl dimethicone, trimethyl silylamodimethicone, etc.

Thickeners

Mascara compositions according to the disclosure may optionally contain thickening or gelling agents. Thickening agents may improve stability, especially at room temperature, and may increase ease of application and curl performance. Such thickening or gelling agents useful herein may optionally include materials which are primarily derived from natural sources. Non-limiting examples of these thickening agents include gums such as acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, biosacharide gum, or mixtures thereof.

Additional non-limiting examples of thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic hetero-polysaccharide derived from callus of plants belonging to Polyantes sp. (for example, tuberous polysaccharide), proteins (for example, sodium casein, gelatin, albumin), chondroitin sulfate, or hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

In certain embodiments, the thickener may be chosen from algin, alginic acid, ammonium alginate, amylopectin, calcium alginate, potassium alginate, propylene glycol alginate, and mixtures thereof. In a preferred embodiment, the thickener is algin.

When present, the thickener may be present in an amount ranging from about 0.001% to about 10%, such as from about 0.005% to about 5%, about 0.01% to about 3%, about 0.01% to about 2%, about 0.01% to about 1%, about 0.05% to about 3%, about 0.05% to about 2%, about 0.05% to about 1%, about 0.1% to about 3%, about 0.1% to about 2%, or about 0.1% to about 1%, including all ranges and sub-ranges there between, based on the total weight of the composition. In certain embodiments, the thickener is present in an amount less than about 1%, such as less than about 0.9%, less than about 0.8%, less than about 0.7%, less than about 0.5%, less than about 0.4%, less than about 0.3%, less than about 0.2%, or less than about 0.1%, relative to the weight of the composition. In yet further embodiments, the at least one thickener may be present in an amount of about 0.05%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, or about 2%, based on the total weight of the composition. In at least certain embodiments, the weight ratio of the total amount of the polyphenol to the total amount of film forming polymer ranges from about 50:1 to about 1:1, 20:1 to about 1:1, 100:1 to about 1:1, 7:1 to about 1:1, about 5:1 to about 1:1, or about 2:1 to about 1:1.

In at least certain embodiments, the compositions are free or substantially free of thickeners.

pH Adjusters

Typically, mascara compositions have a pH greater than about 5. Therefore, mascara compositions according to the disclosure may optionally also contain acid and alkali pH adjusters. Such pH adjusters include, but are not limited to, sodium acetate, sodium metasilicate, silicate compounds, citric acid, ascorbic acid, and carbonate compounds. The disclosed compositions may also be substantially free of acid and alkali pH adjusters.

It may, in at least certain embodiments, be beneficial to adjust the pH of the compositions so that it is approximately at or below the pKa of the polyphenol, or approximately at or below the first pKa of the case of polyphenols having more than one pKa. Without wishing to be bound by theory, adjusting the pH of the composition to be approximately at or below the (first) pKa of the polyphenol may aid in crosslinking of the polymer by the polyphenol. By way of example only, in an embodiment where tannic acid is used, the pH of the disclosed compositions may advantageously be in the range of about 5 to about 8, about 5 to about 7.5, about 5 to about 7, about 5 to about 6.5, or about 5 to about 6.

Vehicle

Mascara compositions according to the disclosure comprise at least one physiologically acceptable medium. The physiologically acceptable medium may be chosen from water or a mixture of water and at least one cosmetically acceptable solvent. Non-limiting examples of cosmetically acceptable solvents include C2-C4 lower alcohols, such as ethanol and isopropanol; polyols, especially those containing from 2 to 6 carbon atoms, for instance glycerol, propylene glycol, butylene glycol, pentylene glycol, hexylene glycol, dipropylene glycol or diethylene glycol; polyol ethers, for instance 2-butoxyethanol, propylene glycol monomethyl ether and diethylene glycol monomethyl ether or monoethyl ether; and mixtures thereof.

In one exemplary embodiment, the mascara composition comprises a vehicle in an amount up to about 99.9%, such as ranging from about 50% to about 99%, about 55% to about 95%, or about 60% to about 90%, by weight relative to the weight of the composition. For example, the composition may comprise water in an amount up to about 99%, such as, for example, an amount ranging from about 40% to about 95%, about 45% to about 90%, or about 50% to about 85%, by weight relative to the weight of the mascara composition.

Additional Components

The compositions according to the disclosure may optionally also comprise additives useful or desired for preparing mascara compositions. Exemplary and non-limiting additives include nacreous agents, dyes or pigments, mineral, plant or synthetic oils, waxes, dispersants, anti-oxidants, preservatives, neutralizing agents, fragrances, fillers, co-solvents, plasticizers, cosmetic and dermatological active agents such as emollients, moisturizers, vitamins, UV filters, sunscreens, and mixtures thereof. Exemplary pigments include A person skilled in the art will take care to select the optional additives and the amount thereof such that they do not harm the properties of the mascara compositions of the present disclosure.

In certain embodiments, these additives are generally present in an amount ranging up to about 40% by weight of active material relative to the total weight of the composition, such as up to about 30%, up to about 20%, up to about 15%, up to about 10%, up to about 5%, such as from 0.01% to 30%.

If desired, a person of skill in the art can select the additives or amounts thereof in order to maintain the desired properties of the compositions.

In certain embodiments, at least 75%, such as at least 80%, at least 85%, at least 90%, or at least 95% of the disclosed materials used in the compositions are plant-based. In one exemplary embodiment, compositions according to the disclosure demonstrate desirable cosmetic properties while comprising mostly, such as at least about 95%, natural origin ingredients.

II. Methods

Methods of making up the eyelashes according to the disclosure comprise applying mascara compositions described herein to the eyelashes. The method by which the mascara compositions is applied to the eyelashes is not limited, and may, for example, be by a brush, a wand, or a comb. The mascara composition may be applied onto the eyelashes in an amount sufficient to coat the eyelashes, to improve the curl of the eyelashes, and/or to improve the thickness, volume, and/or length of the eyelashes. Optionally, the mascara composition may be applied onto the top surface of the top eyelashes, the bottom surface of the bottom eyelashes, the bottom surface of the top eyelashes, and/or the top surface of the bottom eyelashes.

It is to be understood that although mascara compositions and/or processes according to the disclosure generally demonstrate one or more of the properties described herein (e.g. eyelash curling, hold, and/or thickening), compositions according to the disclosure may not demonstrate all or some of the disclosed properties, yet the compositions and methods of making up the eyelashes are still within the scope of the disclosure.

The following definitions are provided for the present disclosure only.

The terms “comprising,” “having,” and “including” (or “comprise,” “have,” and “include”) are used in their open, non-limiting sense. The phrase “consisting essentially of” limits the scope of a claim to the specified materials or steps and those that do not materially affect the basic and novel characteristics of the compositions.

The terms "a," "an," "the," and "at least one" are understood to encompass the plural as well as the singular.

Thus, the term "a mixture thereof" also relates to "mixtures thereof." Throughout the disclosure, if the term "a mixture thereof" is used, following a list of elements as shown in the following example where letters A-F represent the elements: "one or more elements selected from the group consisting of A, B, C, D, E, F, or mixtures thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. The term "about" is used herein to indicate a difference of up to +/−10% from the stated number, such as +/−9%, +/−8%, +/−7%, +/−6%, +/−5%, +/−4%, +/−3%, +/−2%, or +/−1%. Likewise, all endpoints of ranges are understood to be individually disclosed, such that, for example, a range of 1:2 to 2:1 is understood to disclose a ratio of both 1:2 and 2:1.

Unless otherwise indicated, all percentages herein are by weight, relative to the weight of the total composition.

The term "substantially free" or "essentially free" as used herein means the specific material may be present in small amounts that do not materially affect the basic and novel characteristics of the compositions according to the disclosure. For instance, there may be less than 2% by weight of a specific material added to a composition, based on the total weight of the compositions (provided that an amount of less than 2% by weight does not materially affect the basic and novel characteristics of the compositions according to the disclosure. Similarly, the compositions may include less than 2%, less than 1.5%, less than 1%, less than 0.5%, less than 0.1%, less than 0.05%, or less than 0.01%, or none of the specified material. Furthermore, all components that are positively set forth in the instant disclosure may be negatively excluded from the claims, e.g., a claimed composition may be "free," "essentially free" (or "substantially free") of one or more components that are positively set forth in the instant disclosure.

The term "substantially free" or "essentially free" as used herein may also mean that the specific material is not added to the composition but may still be present in a raw material that is included in the composition.

The term "synthetic" means a material that is not of natural origin. The term "natural" means a material of natural origin, such as derived from plants, which also cannot be subsequently chemically or physically modified.

The term "organic" means a material that is produced substantially without or essentially without the use of synthetic materials. The term "substantially without" or "essentially without" as used herein means the specific material may be used in a manufacturing process in small amounts that do not materially affect the basic and novel characteristics of the compositions according to the disclosure. The term "substantially without" or "essentially without" as used herein may also mean that the specific material is not used in a manufacturing process but may still be present in a raw material that is included in the composition.

"Cosmetic composition" encompasses many types of compositions for application to eyelashes, for example, mascara compositions or eyelash enhancing compositions.

It will be apparent to those skilled in the art that various modifications and variations can be made in the compositions and methods according to the disclosure without departing from the spirit or scope of the disclosure. Thus, it is intended that the disclosure cover such modifications and variations and their equivalents.

EXAMPLES

The following examples are intended to be non-limiting and explanatory in nature only.

Example 1

The following mascara compositions were prepared by solubilizing the components in water as disclosed in Table 1 with a 1% sodium acetate buffer to pH 5. Amounts are expressed in wt % of active materials.

TABLE 1

| | Composition | | | | | |
|---|---|---|---|---|---|---|
| | 1a | 1b | 1c | 1d | 1e | 1f |
| Gantrez ® PVM/MA (CAS Number 25153-40-6) | — | 0.1% | — | 0.1% | — | 0.1% |
| Tannic acid | 1.0% | — | — | 1.0% | 1.0% | 1.0% |
| Algin | — | — | 0.1% | — | 0.1% | 0.1% |
| water | Q.S. 100 | Q.S. 100 | Q.S. 100 | Q.S. 100 | Q.S. 100 | Q.S. 100 |
| Degree of curl | 20-40 | 25-35 | 10-30 | 25-50 | 30-50 | 40-70 |

Each of compositions 1a-1f was applied to separate sets of flat, synthetic lashes in 3 applications, each application comprising 10 strokes with a wait time of 2 minutes between each application, using an applicator brush in an upward motion, for a total of 30 strokes per set of eyelashes, with 3 sets of synthetic lashes per composition (i.e. in triplicate). A conventional benchmark mascara composition was also applied to synthetic lashes. The curl of each of the synthetic lashes was then measured (FIG. 1).

Comparative mascara compositions (1b-1c) showed curl ranging from 10-35°. The conventional benchmark mascara composition demonstrated a curl of 20-30°, mascara composition 1b, having no polyphenol, demonstrated a curl of 25-35°, and mascara composition 1c having neither a polyphenol nor a film forming polymer demonstrated a curl of 10-30°.

Compositions according to the disclosure showed curl ranging from 25-70°. Mascara composition 1a having tannic acid but no film forming polymer demonstrated a curl of 20-40°, mascara composition 1d having a combination of tannic acid and Gantrez® PVM/MA demonstrated a curl of 25-50°, composition 1e having tannic acid and thickener (algin) but no film forming polymer demonstrated a curl of 30-50°, and composition 1f having tannic acid, Gantrez® PVM/MA Copolymer, and thickener (algin) demonstrated a curl of 40-70°.

This example demonstrates that mascara compositions comprising a polyphenol, or synergistic combinations of either polyphenol with film forming polymer, polyphenol with thickener, or polyphenol with film-forming polymer and thickener, surprisingly provide improved makeup properties to eyelashes, such as improved curl.

Example 2

The following mascara compositions were prepared by solubilizing the components in water as disclosed in Table 2 with a 1% sodium acetate buffer to pH 5. Amounts are expressed in wt % of active materials.

TABLE 2

| | Composition | | | | | |
|---|---|---|---|---|---|---|
| | 2a | 2b | 2c | 2d | 2e | 2f |
| Gantrez ® PVM/MA (CAS Number 25153-40-6) | — | 0.1% | — | 0.1% | — | 0.1% |
| Tannic acid | 1.0% | — | — | 1.0% | 1.0% | 1.0% |
| Algin | — | — | 0.5% | — | 0.5% | 0.5% |
| water | Q.S. 100 | Q.S. 100 | Q.S. 100 | Q.S. 100 | Q.S. 100 | Q.S. 100 |
| Degree of curl | 20-40 | 20-30 | 10-50 | 40-60 | 10-50 | 20-60 |

Figure 2:
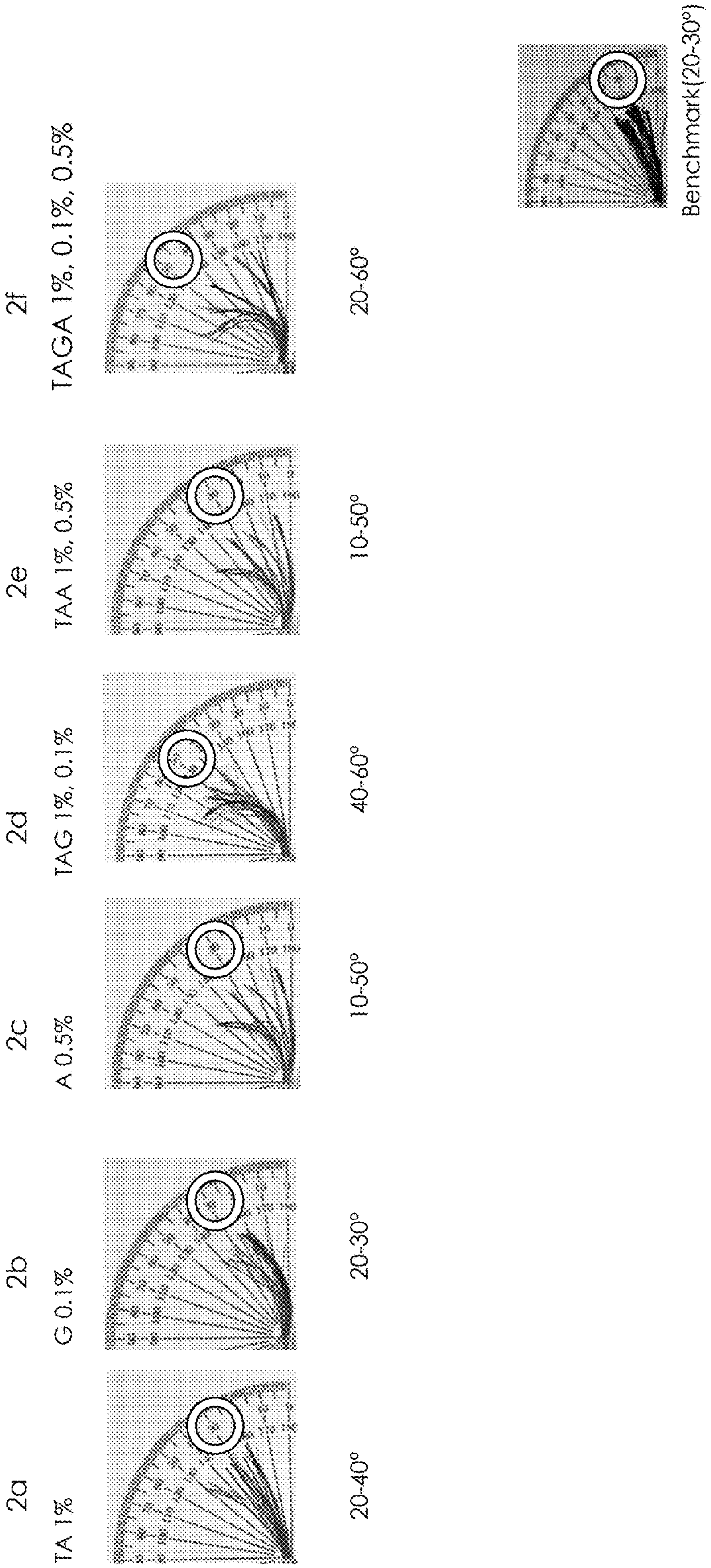
FIG. 2 shows photographs of eyelashes treated with compositions comprising tannic acid, Gantrez® PVM/MA, and/or algin. The eyelashes are aligned with a protractor to measure curliness of the eyelashes.

Each of compositions 2a-2f was applied to separate sets of flat, synthetic lashes in 3 applications, each application comprising 10 strokes with a wait time of 2 minutes between each application, using an applicator brush in an upward motion, for a total of 30 strokes per set of eyelashes, with 3 sets of synthetic lashes per composition (i.e. in triplicate). A conventional mascara composition was also applied to synthetic lashes. The curl of each of the synthetic lashes was then measured (FIG. 2).

Comparative mascara compositions (2b-2c) showed curl ranging from 10-50°. The conventional benchmark mascara composition demonstrated a curl of 20-30°, mascara composition 2b, having no polyphenol, demonstrated a curl of 20-30°, and mascara composition 2c having neither a polyphenol nor a film forming polymer demonstrated a curl of 10-50°.

Compositions according to the disclosure showed curl ranging from 10-60°. Mascara composition 2a having tannic acid but no film forming polymer demonstrated a curl of 20-40°, mascara composition 2d having a combination of tannic acid and Gantrez® PVM/MA demonstrated a curl of 40-60°, composition 2e having tannic acid and thickener (algin) but no film forming polymer demonstrated a curl of 10-50°, and composition 2f having tannic acid, Gantrez® PVM/MA Copolymer, and thickener (algin) demonstrated a curl of 20-60°.

This example demonstrates that mascara compositions comprising a polyphenol, or synergistic combinations of either polyphenol with film forming polymer, polyphenol with thickener, or polyphenol with film-forming polymer and thickener, surprisingly provide improved makeup properties to eyelashes, such as improved curl.

Example 3

The following mascara compositions were prepared by solubilizing the components in water as disclosed in Table 3 with a 0.5% sodium acetate buffer to pH 5. Amounts are expressed in wt % of active materials.

TABLE 3

| | Composition | | | | | |
|---|---|---|---|---|---|---|
| | 3a | 3b | 3c | 3d | 3e | 3f |
| Carrageenan | — | 0.1% | — | 0.1% | — | 0.1% |
| Tannic acid | 1.0% | — | — | 1.0% | 1.0% | 1.0% |
| Algin | — | — | 0.1% | — | 0.1% | 0.1% |
| water | Q.S. 100 | Q.S. 100 | Q.S. 100 | Q.S. 100 | Q.S. 100 | Q.S. 100 |
| Degree of curl | 30-40 | 20-40 | 0-15 | 30-50 | 40-60 | 60-80 |

Figure 3:
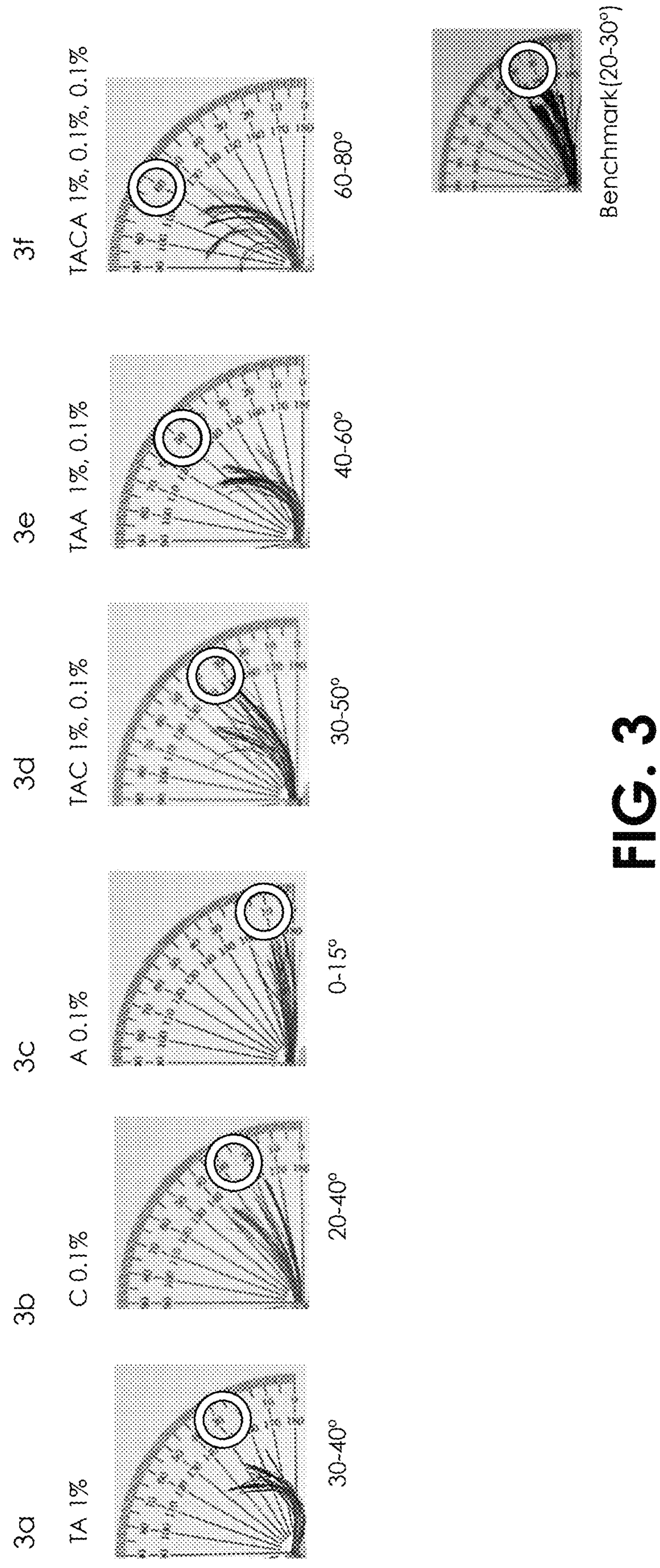
FIG. 3 shows photographs of eyelashes treated with compositions comprising tannic acid, carrageenan, and/or algin. The eyelashes are aligned with a protractor to measure curliness of the eyelashes.

Each of compositions 3a-3f was applied to separate sets of flat, synthetic lashes in 3 applications, each application comprising 10 strokes with a wait time of 2 minutes between each application, using an applicator brush in an upward motion, for a total of 30 strokes per set of eyelashes, with 3 sets of synthetic lashes per composition (i.e. in triplicate). A conventional mascara composition was also applied to synthetic lashes. The curl of each of the synthetic lashes was then measured (FIG. 3).

Comparative mascara compositions (3b-3c) showed curl ranging from 0-40°. The conventional mascara composition demonstrated a curl of 20-30°, mascara composition 3b, having no polyphenol, demonstrated a curl of 20-40°, and mascara composition 3c having neither a polyphenol nor a film forming polymer demonstrated a curl of 0-15°.

Compositions according to the disclosure showed curl ranging from 30-80°. Mascara composition 3a having tannic acid but no film forming polymer demonstrated a curl of 30-40°, mascara composition 3d having a combination of tannic acid and carrageenan demonstrated a curl of 30-50°, composition 3e having tannic acid and thickener (algin) but no film forming polymer demonstrated a curl of 40-60°, and composition 3f having tannic acid, carrageenan, and thickener (algin) demonstrated a curl of 60-80°.

This example demonstrates that mascara compositions comprising a polyphenol, or synergistic combinations of either polyphenol with film forming polymer or polyphenol, polyphenol with thickener, or polyphenol with film-forming polymer and thickener, surprisingly provide improved makeup properties to eyelashes, such as improved curl.

Example 4

The following mascara compositions were prepared by solubilizing the components in water as disclosed in Table 4 with a 0.5% sodium acetate buffer to pH 5. Amounts are expressed in wt % of active materials.

TABLE 4

| | Composition | | | | | |
|---|---|---|---|---|---|---|
| | 4a | 4b | 4c | 4d | 4e | 4f |
| Carrageenan | — | 0.2% | — | 0.2% | — | 0.2% |
| Tannic acid | 1.0% | — | — | 1.0% | 1.0% | 1.0% |
| Algin | — | — | 0.1% | — | 0.1% | 0.1% |
| water | Q.S. 100 | Q.S. 100 | Q.S. 100 | Q.S. 100 | Q.S. 100 | Q.S. 100 |
| Degree of curl | 20-40 | 30-40 | 15-20 | 40-60 | 40-60 | 50-80 |

Figure 4:
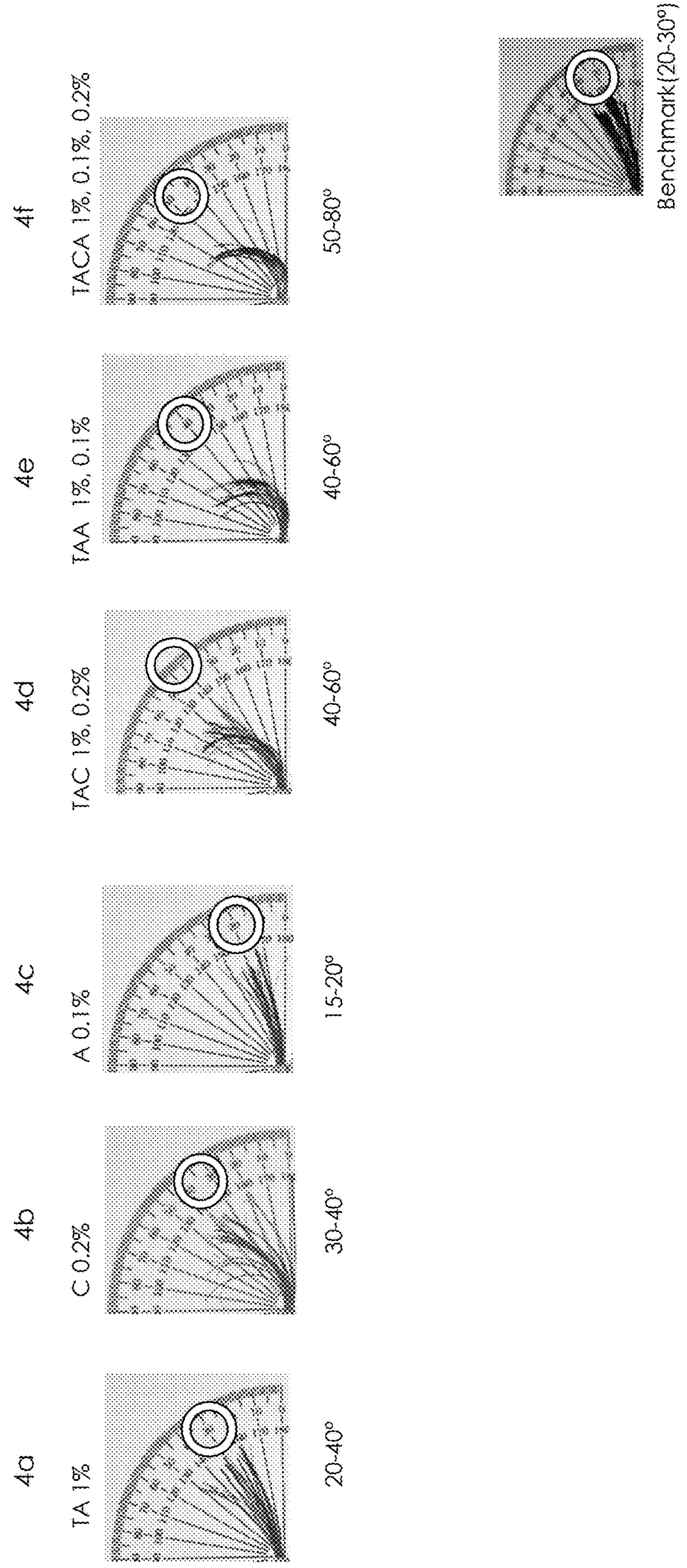
FIG. 4 shows photographs of eyelashes treated with compositions comprising tannic acid, carrageenan, and/or algin. The eyelashes are aligned with a protractor to measure curliness of the eyelashes.

Each of compositions 4a-4f was applied to separate sets of flat, synthetic lashes in 3 applications, each application comprising 10 strokes with a wait time of 2 minutes between each application, using an applicator brush in an upward motion, for a total of 30 strokes per set of eyelashes, with 3 sets of synthetic lashes per composition (i.e. in triplicate). A conventional mascara composition was also applied to synthetic lashes. The curl of each of the synthetic lashes was then measured (FIG. 4).

Comparative mascara compositions (4b-4c) showed curl ranging from 15-40°. The conventional benchmark mascara composition demonstrated a curl of 20-30°, mascara composition 4b, having no polyphenol, demonstrated a curl of 30-40°, and mascara composition 4c having neither a polyphenol nor a film forming polymer demonstrated a curl of 15-20°.

Compositions according to the disclosure showed curl ranging from 20-80°. Mascara composition 4a having tannic acid but no film forming polymer demonstrated a curl of 20-40°, mascara composition 4d having a combination of tannic acid and carrageenan demonstrated a curl of 40-60°, composition 4e having tannic acid and thickener (algin) but no film forming polymer demonstrated a curl of 40-60°, and composition 4f having tannic acid, carrageenan, and thickener (algin) demonstrated a curl of 50-80°.

This example demonstrates that mascara compositions comprising a polyphenol, or synergistic combinations of either polyphenol with film forming polymer, polyphenol with thickener, or polyphenol with film-forming polymer and thickener, surprisingly provide improved makeup properties to eyelashes, such as improved curl.

Example 5

The following mascara compositions were prepared by solubilizing the components disclosed in Tables 5 and 6 in water. Amounts are expressed in wt % of active materials.

TABLE 5

| | Composition | | |
|---|---|---|---|
| Ingredient | 5a | 5b | 5c |
| Tannic Acid (%) | 1.250 | 1.250 | 2.000 |
| Carrageenan (%) | 0.125 | 0.200 | 0.200 |
| Alginate (%) | 0.125 | 0.125 | 0.125 |
| Ethanol (%) | 4.000 | 7.000 | 1.000 |
| Caprylyl Glycol (%) | 0.300 | 0.300 | 0.300 |
| Phenoxyethanol (%) | 0.300 | 0.300 | 0.300 |
| Iron Oxides (%) | 7.000 | 7.000 | 7.000 |
| Deionized Water | q.s. | q.s. | q.s. |
| Average Curl (Degree) | 77 | 87 | 83 |

TABLE 6

| | Composition | | |
|---|---|---|---|
| Ingredient | 6a | 6b | 6c |
| Tannic Acid (%) | 1.250 | 1.250 | 2.000 |
| Carrageenan (%) | 0.125 | 0.200 | 0.200 |
| Alginate (%) | 0.125 | 0.125 | 0.125 |
| Ethanol (%) | 4.000 | 7.000 | 1.000 |
| Caprylyl Glycol (%) | 0.300 | 0.300 | 0.300 |
| Phenoxyethanol (%) | 0.300 | 0.300 | 0.300 |
| Carbon Black (%) | 1.000 | 1.000 | 1.000 |
| Deionized Water | q.s. | q.s. | q.s. |
| Average Curl (Degree) | 63 | 77 | 83 |

Artificial eyelashes were prepared by washing 1 time. Eyelash samples were subsequently taped together (so there are two parallel rows of lashes) and flat-ironed 10 times to ensure the lashes were straight.

Each of compositions 5a-5c and 6a-6c was applied to separate sets of flat, synthetic lashes in 6 applications, each application comprising 10 strokes with a wait time of 2 minutes between each application, using an applicator brush in an upward motion, for a total of 60 strokes per set of eyelashes. The curl of each of the synthetic lashes was then measured. It was observed that curl performance was maintained in the presence of common mascara ingredients (pigments, preservatives, etc.).

This example demonstrates that mascara compositions comprising synergistic combinations of a polyphenol, film forming polymer, thickener, and pigment surprisingly provide improved makeup properties to eyelashes, such as improved curl.

Samples 6a, 6b, and 6c were further placed into a humidity-controlled chamber at 80% relative humidity and 23° C. for 1 hour. It was observed that the initial imparted curl to the eyelash sample was retained through the duration of the experiment.

The invention claimed is:

1. A mascara composition comprising:

a. at least one polyphenol comprising tannic acid, in an amount of about 0.1% to about 3%, and b. at least one film forming polymer in an amount of about 0.05% to about 1%, wherein the pH of the composition is approximately at or below the pKa of the polyphenol, wherein the weight ratio of the total amount of the polyphenol to the total amount of film forming polymer ranges from about 20:1 to about 1:1, and wherein the mascara composition is an eyelash-curling mascara composition.

2. The mascara composition of claim 1, wherein the at least one film forming polymer is chosen from acrylate-based polymers, polyurethanes, polysaccharides, or mixtures thereof.

3. The mascara composition of claim 1, wherein the at least one film forming polymer is chosen from PVM/MA Copolymer, carrageenan, gum Arabic, xanthan gum, alginate, or mixtures thereof.

4. The mascara composition of claim 1, wherein the weight ratio of the total amount of the polyphenol to the total amount of film forming polymer ranges from about 5:1 to about 1:1.

5. The mascara composition of claim 1, further comprising at least one thickener.

6. The mascara composition of claim 1, where the at least one thickener is present in an amount ranging from about 0.005% to about 5%.

7. The mascara composition of claim 1, where the at least one thickener is present in an amount ranging from about 0.05% to about 2%.

8. The mascara composition of claim 1, wherein the weight ratio of the total amount of the polyphenol to the total amount of thickener ranges from about 10:1 to about 1:1.

9. The mascara composition of claim 1, wherein the weight ratio of the total amount of the polyphenol to the total amount of thickener ranges from about 2:1 to about 1:1.

10. The mascara composition of claim 1, wherein the at least one thickener is chosen from gums, water-soluble natural polymers, water-soluble synthetic polymers, clay minerals, silicic anhydride, or mixtures thereof.

11. The mascara composition of claim 1, wherein the at least one thickener is algin.

12. The mascara composition of claim 1, wherein the composition further comprises pigment.

13. The mascara composition of claim 1, wherein the at least one polyphenol is tannic acid, and the at least one film forming polymer is chosen from carrageenan or the polymers of formula (I):

$$[CH_2CH(OCH_3)CH(CO_2H)CH(CO_2H)]n \quad (I),$$

wherein n is a number from about 2,500 to about 17,500, wherein the pH of the composition is from about 5 to about 6.

* * * * *